United States Patent
Zayed et al.

(10) Patent No.: US 11,369,381 B2
(45) Date of Patent: Jun. 28, 2022

(54) TAILORED VENOUS ANASTOMOSIS FOR ARTERIOVENOUS GRAFTS

(71) Applicant: Washington University, St. Louis, MO (US)

(72) Inventors: Mohamed Zayed, St. Louis, MO (US); Dillon Williams, St. Louis, MO (US); Guy Genin, St. Louis, MO (US); Eric Leuthardt, St. Louis, MO (US)

(73) Assignee: Washington University, St. Louis, MO (US)

( * ) Notice: Subject to any disclaimer, the term of this patent is extended or adjusted under 35 U.S.C. 154(b) by 41 days.

(21) Appl. No.: 16/920,221

(22) Filed: Jul. 2, 2020

(65) Prior Publication Data
US 2021/0000471 A1 Jan. 7, 2021

Related U.S. Application Data

(60) Provisional application No. 63/004,314, filed on Apr. 2, 2020, provisional application No. 62/869,708, filed on Jul. 2, 2019.

(51) Int. Cl.
*A61B 17/11* (2006.01)

(52) U.S. Cl.
CPC ....... *A61B 17/11* (2013.01); *A61B 2017/1107* (2013.01)

(58) Field of Classification Search
CPC ............ A61B 17/11; A61B 2017/1132; A61B 2017/1135; A61B 2017/1139; A61B 2017/1107
See application file for complete search history.

(56) References Cited

U.S. PATENT DOCUMENTS

| 6,001,124 A | 12/1999 | Bachinski |
| 6,585,762 B1 | 7/2003 | Stanish |
| 2004/0064081 A1 | 4/2004 | Stanish |
| 2005/0192604 A1 | 9/2005 | Carson et al. |
| 2006/0064119 A9 | 3/2006 | Tilson et al. |
| 2008/0294245 A1* | 11/2008 | Lundh ...................... A61F 2/06 623/1.35 |
| 2014/0194910 A1* | 7/2014 | Orion .................. A61M 1/3655 606/153 |

OTHER PUBLICATIONS

Williams, D. et al., "A Novel Design for Shear Rate Optimization of the Venous-End Anastomosis of an Arteriovenous Graft," Arteriosclerosis, Thrombosis, and Vascular Biol., Jul. 2019, 1 pg., vol. 39, Abstract 272.

* cited by examiner

*Primary Examiner* — Diane D Yabut
*Assistant Examiner* — Christina C Lauer
(74) *Attorney, Agent, or Firm* — Polsinelli, PC

(57) ABSTRACT

An arteriovenous graft and methods of reducing the risk of graft thrombosis and extending patency of the arteriovenous graft are provided herein. The arteriovenous graft is operable for attaching to a vein at a venous anastomosis. In some aspects, the arteriovenous graft includes a plurality of grooves at a venous anastomosis end of the arteriovenous graft and the venous anastomoses may be arranged such that the arteriovenous graft and the vein meet at an angle of 30° or less.

14 Claims, 21 Drawing Sheets
(17 of 21 Drawing Sheet(s) Filed in Color)

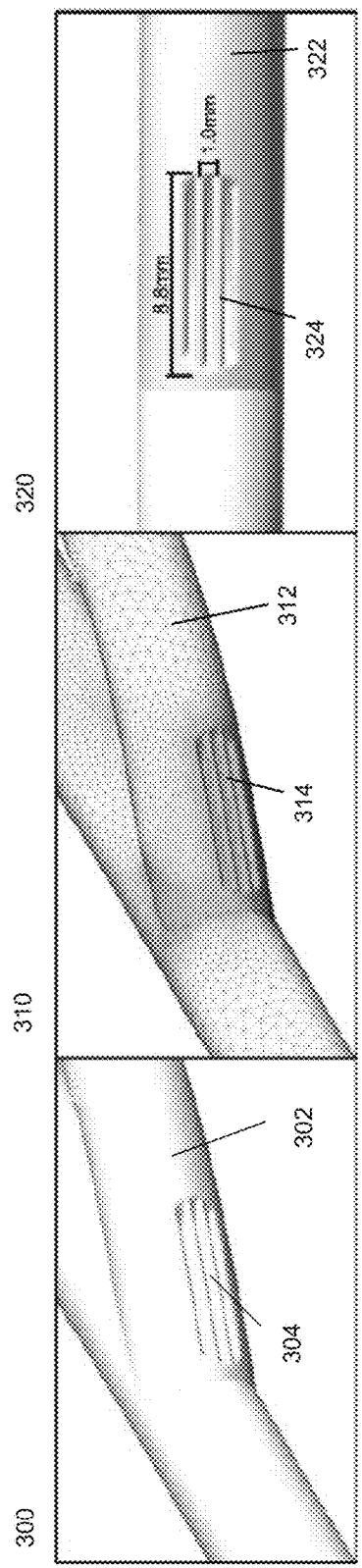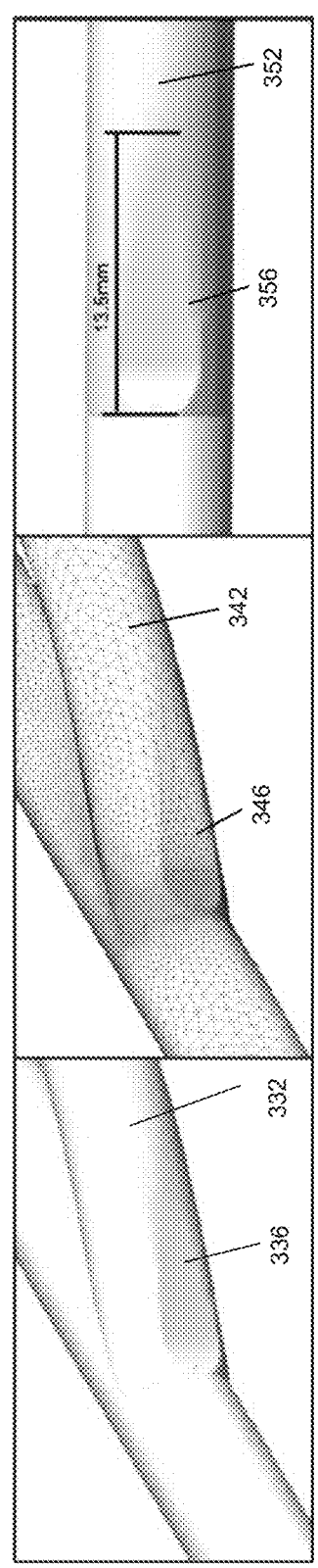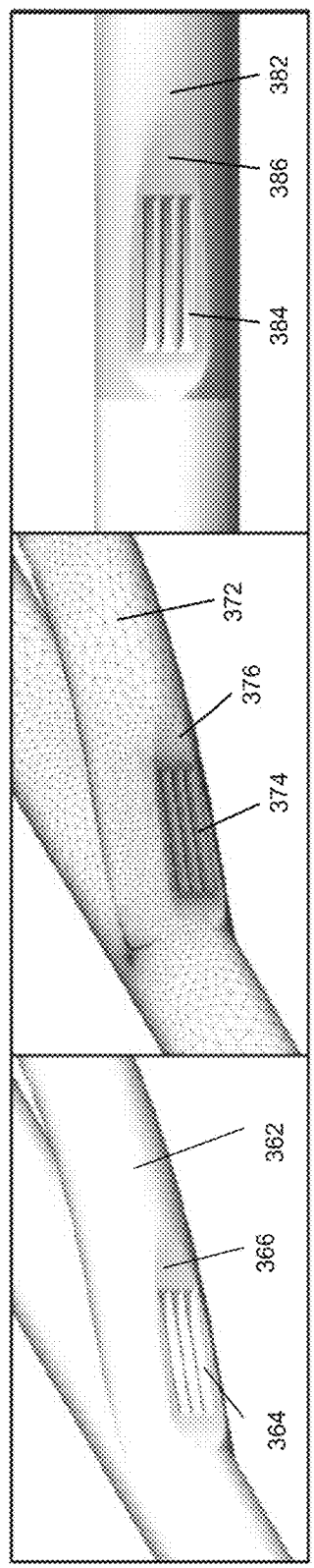

US 11,369,381 B2

TAILORED VENOUS ANASTOMOSIS FOR ARTERIOVENOUS GRAFTS

CROSS-REFRENCE TO RELATED APPLICATIONS

This application claims priority to U.S. Provisional Patent Application 62/869,708, which was filed in the U.S. Patent and Trademark Office on Jul. 2, 2019, and U.S. Provisional Patent Application 63/004,314, which was filed in the U.S. patent and Trademark Office on Apr. 2, 2020, each of which are incorporated herein by reference in their entirety for all purposes.

GOVERNMENTAL RIGHTS

This invention was made with government support under CMMI1548571 from the National Science Foundation. The government has certain rights in the invention. This work was supported by the U.S. Department of Veterans Affairs, and the Federal Government has certain rights in this invention.

FIELD

The present disclosure is directed to arteriovenous grafts used for hemodialysis. In at least one example, the present disclosure relates to arteriovenous grafts with a tailored venous anastomosis.

BACKGROUND

Gradual loss of kidney function can lead to end stage renal disease, in which the kidneys are no longer able to filter from the arterial blood stream toxic metabolites, electrolytes, and excess fluid. Accordingly, patients with end stage renal disease require artificial means for blood stream filtration, such as hemodialysis. Hemodialysis may include placement of a subcutaneous non-autogenous artificial arteriovenous graft. Arteriovenous grafts used for hemodialysis have a high rate of failure due to stenosis at the venous-end anastomosis.

Failed and obstructed arteriovenous grafts lead to acute loss of dialysis access, increased patient morbidity, and high associated medical costs. One of the main causes of failures and complications at the venous-end anastomosis is formation of thrombus. There is therefore a pressing need for improvement of arteriovenous graft longevity, particularly the longer-term patency of the venous-end anastomosis of arteriovenous grafts.

As presented herein, an arteriovenous graft can be optimized to reduce the risk of graft thrombosis and extend patency.

BRIEF SUMMARY

Provided herein is an arteriovenous graft operable for attaching to a vein at a venous anastomosis. The arteriovenous graft may include a plurality of grooves at a venous anastomosis end of the arteriovenous graft and the venous anastomoses may have an angle of 30° or less.

Further provided herein is a method of reducing the risk of graft thrombosis and extend patency of an arteriovenous graft. The method may include attaching a venous anastomosis end of the arteriovenous graft to a vein at a venous anastomosis and attaching an arterial anastomosis end of the arteriovenous graft to an artery at a venous anastomosis. The arteriovenous graft may include a plurality of grooves at the venous anastomosis end, and the venous anastomoses may have an angle of 30° or less.

Other aspects and iterations of the invention are described more thoroughly below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description will be more fully understood with reference to the following figures and data graphs, which are presented as various embodiments of the disclosure and should not be construed as a complete recitation of the scope of the disclosure, wherein:

FIGS. 3A-3C show three iterations of the tailored anastomosis shown alongside their respective meshing regime and dimensions. FIG. 3A shows the micro-digit grooves. FIG. 3B shows the lachrymiform indent. FIG. 3C shows the combination of the two features.

FIG. 6A shows total data for six different venous anastomosis configurations. FIG. 6B shows the pathologically low shear strain rate range within the vein wall. FIG. 6C shows the physiologically healthy range of wall shear rate within the vein. FIG. 6D shows the pathologically high shear strain rate within the vein wall.

FIG. 7A shows just the microdigit groves. FIG. 7B shows just the lachrymiform indent. FIG. 7C shows the combination of the features for the fully optimized graft.

FIG. 8A shows total data for the four different venous anastomoses. FIG. 8B shows the pathologically low shear strain rate range within the vein wall. FIG. 8C shows the physiologically healthy range of wall shear rate within the vein. FIG. 8D shows the pathologically high shear strain rate within the vein wall.

FIG. 12A shows measurements at 0.1 seconds through the heartbeat, where excessive high shear rate for all venous-end anastomosis anglers considered occurs. FIG. 12B shows measurements 0.3 seconds through the heartbeat, where excessive low shear rate for all venous-end anastomosis angles considered occurs.

DETAILED DESCRIPTION

Figure 1A:
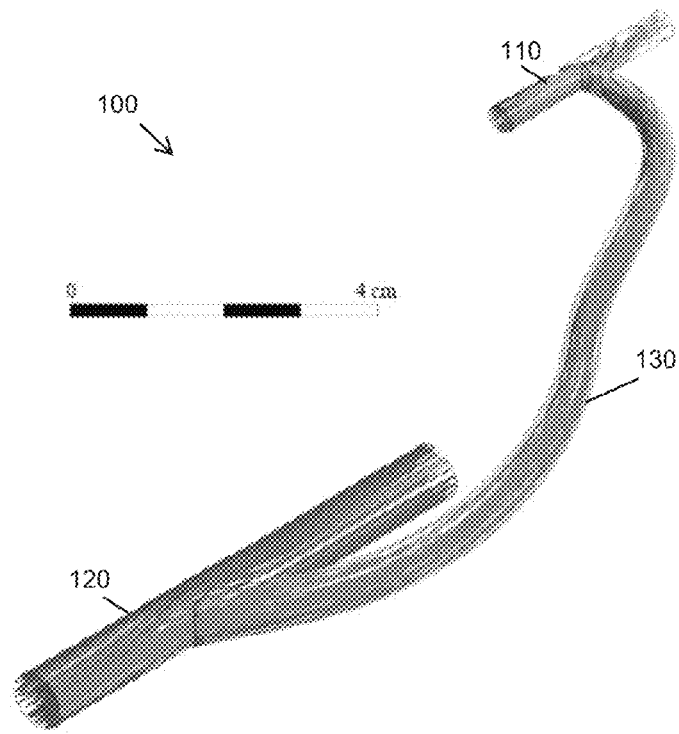
FIG. 1A shows an idealized model of an arteriovenous graft. For illustration, streamlines estimated by computational fluid dynamics analysis are shown: red streamlines represent arterial blood flow, and blue streamlines represent venous blood flow.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The terms "coupled" or "attached" defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described.

Figure 1B:
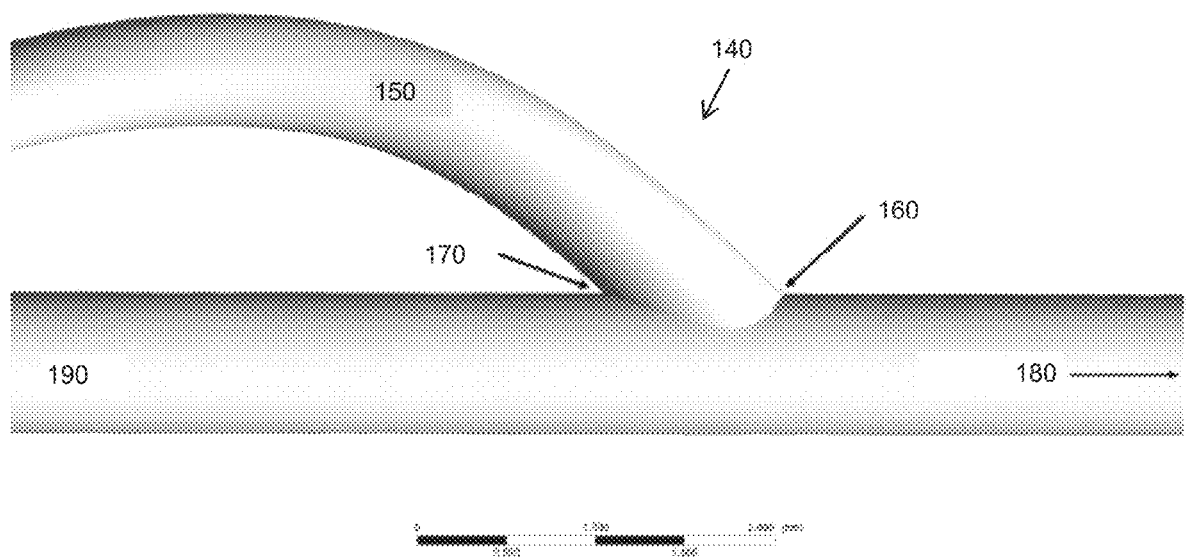
FIG. 1B shows a venous anastomosis demonstrating the beveled hood of the venous-end of the arteriovenous graft.

Life-sustaining procedures which facilitate the removal of metabolic toxins from a patient's blood stream can include diverting arterial blood to a dialyzer, and then returning the blood to the venous blood stream. In at least one instance, arteriovenous grafts can be placed in the patient to provide access to the patient's arterial and venous blood streams. FIGS. 1A and 1B illustrate an exemplary arteriovenous graft connecting an arterial and venous blood stream. Specifically, arteriovenous grafts in the upper extremity are typically placed in two major configurations: either as a brachial artery to axillary vein (brachio-axillary) upper arm graft as illustrated in FIG. 1A, or brachial artery to brachial/cephalic vein loop graft in the forearm, not illustrated. Specifically, FIG. 1A illustrates an arteriovenous graft 100 which couples an arterial blood flow 110 to a venous blood flow 120 with a graft 130. The brachial artery range in diameter is 3 to 5 mm, and the maximum blood flow velocity ranges from 60 cm/s to 100 cm/s. The axillary vein diameter ranges from 6 to 10 mm, and has a mean blood flow velocity of approximately 15 cm/s. It is generally preferred that arteriovenous grafts be implanted in a tapered tube configuration with a 4 mm end used for the arterial anastomosis to limit the steal of arterial blood from the peripheral limb. The other end may be 7 mm and is typically beveled by the surgeon to increase the circumference of the graft venous anastomosis. A detailed view of an exemplary arteriovenous graft 140 is shown in FIG. 1B. As illustrated, the graft 150 is connected to the vein having a proximal 180 and a distal end 190. In at least one instance, the graft 150 can include a tapered conduit as described above. The graft 150 can be coupled with the vein at an angle such that the toe 160 and heel 170 of the graft 150 are beveled.

Failure rates of brachio-axillary arteriovenous grafts are as high as 30% within the first 12 months. Such failure can cause acute loss of hemodialysis access and can increase patient morbidity. As many as 70% of arteriovenous grafts have complications due to reduced flow associated with stenosis that gradually occurs at the venous-end anastomosis of the arteriovenous graft.

One of the main causes of failures and complications at the venous-end anastomosis is formation of thrombus. A key catalyst for thrombus formation is shear along the adjacent vein wall at rates that are either above or below the physiological range. Shear strain rates below the threshold of 50 $s^{-1}$ show increased fibrin deposition that stimulate coagulation cascades are greatly increased, and reduced clearance of coagulation factors at sites of vascular injury. On the other hand, shear rates elevated above 1000 $s^{-1}$ at the site of vascular injury can lead to platelet aggregation, platelet adherence to subendothelial von Willebrand factor by surface glycoprotein lb receptor, and rapid stimulation of the coagulation cascade leading to large thrombus formation. Maintaining appropriate flow rates within physiological range at the graft-to-vein anastomosis in order to maintain graft patency.

Another aspect which can have significant effect on the wall shear stress of the graft is the angle at which the graft joins the vein. As provided herein, altering the anastomosis angle and the graft wall properties of the venous-end of a brachio-axillary arteriovenous graft may alter aberrant flow fields in this problematic area. The arteriovenous graft provided herein is optimized to the risk of graft thrombosis and extend patency by altering the venous-end anastomosis angle and adding features to the graft wall to alter the incidence of pathological vein shear strain fields. Also provided herein is a method reduce the risk of graft thrombosis, to extend patency, and/or to further alleviate shear rates at the venous-end anastomosis.

Provided herein is an arteriovenous graft for attaching to a vein at a venous anastomosis angle which provides optimum results. In various examples, the arteriovenous graft is a subcutaneous non-autogenous artificial arteriovenous graft. At one end the graft is anastomosed to an extremity artery and on the other end it is anastomosed to an adjacent extremity vein. The body of the graft is then percutaneously cannulated during hemodialysis sessions.

In at least one instance, the arteriovenous graft may have an anastomosis angle of 30° or less and a graft end geometry that may impact blood shear rate on the adjacent venous wall. In at least one instance, the arteriovenous graft may include a cuff or beveled attachment point to the venous end of an arteriovenous graft that may mitigate unhealthy wall shear rate of blood entering the vein from the graft.

The venous end anastomosis angle of the venous-end of brachio-axillary arteriovenous grafts is associated with pathologically high and/or pathologically low wall shear strain rates. In at least one instance, a venous anastomosis angle of greater than 30° may be associated with pathological boundary layer separation and high shear strain rates. Reducing the angle of the venous-end anastomosis may significantly improve the shear strain rates. In at least some instances, the angle of the venous anastomoses near the insertion of the arteriovenous graft may be tailored to reduce the vein wall area over which pathologically high and/or pathologically low shear strain rates occur. In accordance with the present disclosure, the venous anastomoses, where the arteriovenous graft attaches to the vein, may have an angle of about 30°. In at least some instances, the angle of venous anastomosis is less than 30°, for example 15° or less or 13° or less. In at least some instances, the venous end of the arteriovenous graft may be pre-cut or pre-formed to the venous anastomosis angle.

Figure 2:
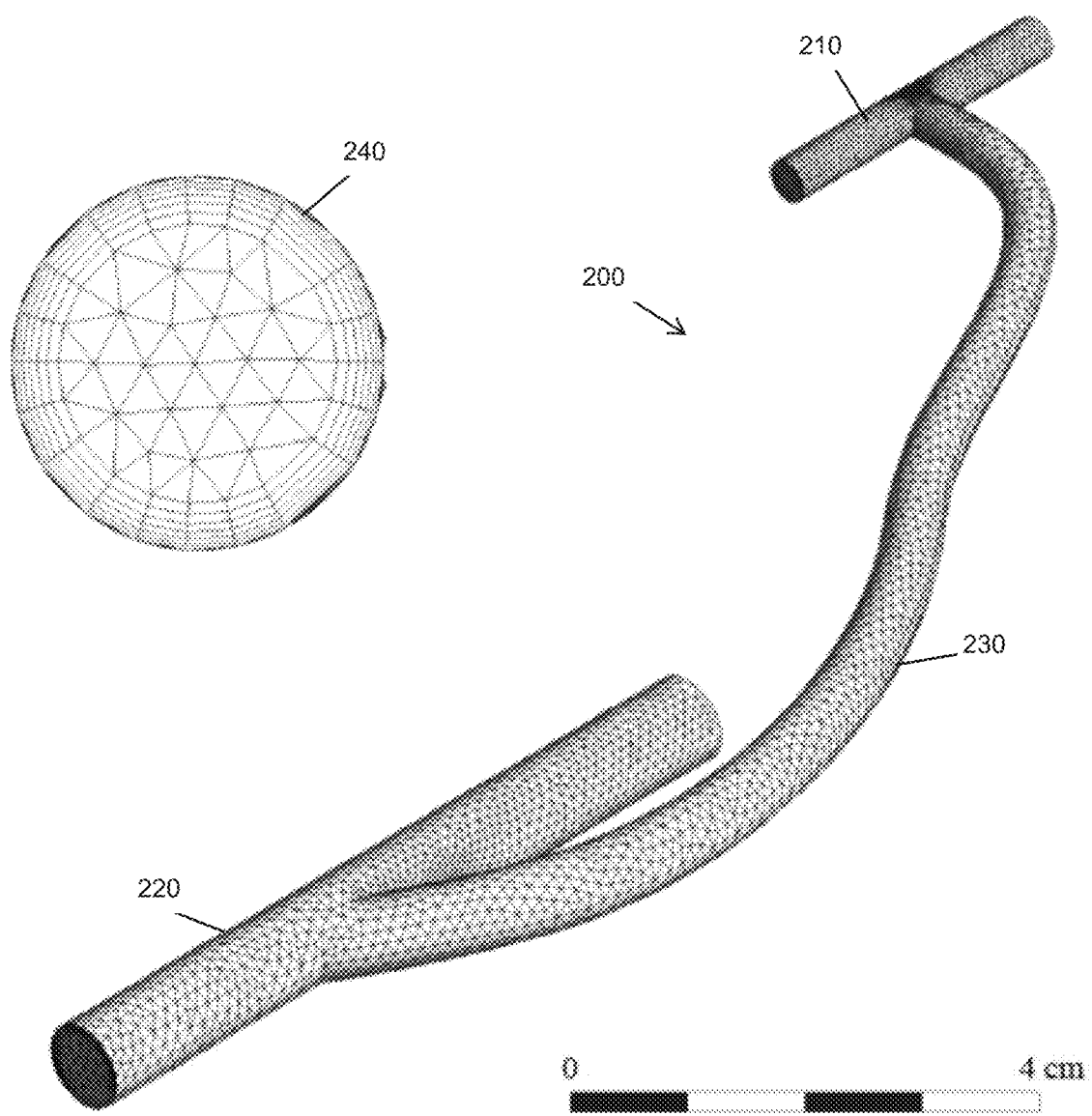
FIG. 2 shows the mesh of the simple arteriovenous model used. The smaller diameter cylinder is the artery, and the larger diameter cylinder is the vein. The two were connected by an arteriovenous graft. Shown is a model with a 30° venous anastomosis. The inset is a close up of the venous outlet that shows the mesh refinement at the boundary layer.

The arteriovenous graft as described herein can be made of various biocompatible materials. In at least one instance, as illustrated in FIG. 2, the arteriovenous graft model 200 can be modeled using a mesh. As illustrated, the arteriovenous graft model 200 can include an arterial blood flow 210 and a venous blood flow 220 coupled to one another via a graft 230. A cross-sectional view 240 of the venous outlet of the arteriovenous graft model 200 is provided showing the mesh refinement at the boundary layer.

Various configurations of arteriovenous grafts are illustrated in FIGS. 3A-3C. Specifically, FIG. 3A illustrates images 300, 310, 320 of an arteriovenous graft 302 that may include a plurality of grooves 304 at a venous anastomosis end of the arteriovenous graft 302. In at least one instance, the plurality of grooves 304 can be inlaid micro-digit grooves. Such grooves may be tailored to reduce the vein wall area over which pathologically high and/or pathologically low shear strain rates occur near the insertion of the graft 302. Image 310 illustrates a meshing regime having an arteriovenous graft 312 including a plurality of grooves 314. Image 320 illustrates the arteriovenous graft 322 and plurality of grooves 324, specifically showing the dimensions of the grooves 324. In at least one instance, the arteriovenous graft 302, 312, 322 may include at least three grooves 304, 314, 324 at the venous anastomosis end of the arteriovenous graft 302, 312, 322. The micro-digit grooves 304, 314, 324 may have a width of about 0.5 mm to about 5 mm, about 1 mm to about 3 mm, about 2 mm to about 4 mm, or about 3 mm to about 5 mm. In another instance, the micro-digit grooves 304, 314, 324 may have a width of about 1 mm. The micro-digit grooves 304, 314, 324 may have a length of about 1 mm to about 10 mm, about 3 mm to about 5 mm, about 5 mm to about 7 mm, about 6 mm to about 8 mm, about 7 mm to about 9 mm, or about 8 mm to about 10 mm. In at least one instance, the micro-digit grooves 304, 314, 324 have a length of about 8.8 mm.

FIG. 3B illustrates images 330, 340, 350 showing alternative tailored anastomosis in accordance with the present disclosure. For example, in some instances, the arteriovenous graft 332, 342, 352 may include a lachrymiform, or tear shaped, indent 336, 346, 356 at the venous anastomosis end. Image 340 illustrates a mesh regime of an arteriovenous graft 342 having a lachrymiform indent 346. Image 350 illustrates the size of a lachrymiform indent 356 that can be present on an arteriovenous graft 352 in accordance with the present disclosure. In at least one instance, the lachrymiform indent may have a length of about 1 mm to about 15 mm, about 2 mm to about 6 mm, about 4 mm to about 8 mm, about 6 mm to about 10 mm, about 8 mm to 12 mm, or about 10 mm to about 15 mm. In another instance, the lachrymiform indent has a length of about 13.5 mm.

Finally, FIG. 3C illustrates a series of images 360, 370, 380 showing an arteriovenous graft 362, 372, 382, having both a plurality of 364, 374, 384 and a lachrymiform indent 366, 376, 386. In at least one instance, the plurality of grooves 364, 374, 384 may be inset within the lachrymiform indent 366, 376, 386.

The plurality of grooves and/or lachrymiform indent function to alter the flow field of the incoming arterial blood to more closely resemble the venous blood in both direction and velocity. Such features may further optimize the prevalence of pathological wall shear strain rates. The tailored anastomosis can greatly reduce the unhealthy high and low shear strain rate on the vein wall compared to a simple anastomosis, as shown and described in greater detail with respect to FIGS. 7A-7C and 8A-8D. The reduction in unhealthy wall shear rate may lead to a lower instance of thrombosis at the venous anastomosis.

The arteriovenous graft as described herein may be made of a biocompatible material, including but not limited to, polytetrafluoroethylene (PTFE), polyurethane (PU), polyethylene terephthalate (PET), polyacrylnitrile (PAN), and any other biocompatible material capable of achieving the desired flow. The arterial end of the arteriovenous graft may have a diameter ranging from about 3 mm to about 5 mm. The venous end of the arteriovenous graft may have a diameter of about 6 mm to about 10 mm. In at least one instance, the arteriovenous graft may have a diameter that tapers from 4 mm at an arterial anastomosis end to 7 mm at the venous anastomosis end. In some instances, the arteriovenous graft may have a length of about 50 mm to about 200 mm, about 50 mm to about 100 mm, about 75 mm to about 125 mm, about 100 mm to about 150 mm, about 125 mm to about 175 mm, and about 150 mm to about 200 mm. In at least one instance, the arteriovenous graft has a length of about 148 mm to about 152 mm. In at least one instance, the length of the arteriovenous graft can depend at least in part on the venous-end anastomosis angle of attachment at the artery. As described in further detail herein, the range of venous anastomosis configurations which can be utilized by a surgeon can include venous attachments at 90°, 60°, 45°, 30°, 15°, and 13° angles. In some instances, the venous anastomosis has a semi major axis of about 15 mm to 30 mm for anastomosis angles of 30° to 15°, respectively.

The shear strain rate fields at the venous end anastomosis play an important role in maintaining arteriovenous graft patency. As discussed above, shear rates above and below the physiological healthy range can lead to thrombosis formation and can result in a compromised graft. The surgical implantation of a non-autogenous graft creates an environment that is already at risk for adjacent wall inflammation and shear strain rates in the pathological range. Therefore, it is clear that the venous end graft anastomosis plays an important role in the prevalence of pathologically high and low shear strain rates and the incidence of vorticity. By optimizing the angle at which the arteriovenous graft is attached, these deleterious variables can be minimized. Modification of the venous-end anastomosis, such as including a plurality of ventral hood grooves and/or a lachrymiform indent may further decrease the occurrence of the unhealthy flow phenomena described herein. In at least one instance, the arteriovenous graft as disclosed herein has a lower high shear rate than a standard arteriovenous graft, having a 90° angle of venous anastomosis. In another example, the arteriovenous graft has a lower low shear rate than a standard arteriovenous graft with a 90° angle of venous anastomosis.

Provided herein is a method for enhancing graft patency and/or reducing the risk of graft thrombosis following arteriovenous graft implantations. The method may include attaching a venous anastomosis end of the arteriovenous graft to a vein an arterial anastomosis end of the arteriovenous graft to an artery, where the arteriovenous graft includes a plurality of grooves at the venous anastomosis end, and the venous anastomoses has an angle of 30° or less.

As described above, the plurality of grooves on the arteriovenous graft may be micro-digit grooves. In the alternative, or in addition to the plurality of grooves, the arteriovenous graft may include a lachrymiform indent at the venous anastomosis end. In at least one instance, the angle of venous anastomosis may be 15° or less. An arteriovenous graft as described herein may have a lower high shear rate than a standard arteriovenous graft, such as one having a 90° angle of venous anastomosis. Additionally, the arteriovenous graft as described herein may have a lower low shear rate than a standard arteriovenous graft, having a 90° angle of venous anastomosis.

The following examples are provided to illustrate the subject matter of the present disclosure. The examples are not intended to limit the scope of the present disclosure and should not be so interpreted.

EXAMPLES

Example 1: Computational Fluid Dynamics (CFD) Simulations

A series of simulations were performed to determine the pulsatile flow field of blood in a brachio-axillary arteriovenous graft system with a graft. The flow of the simulations was estimated through pressure-based, transient computational fluid dynamics (CFD) simulations. An estimate of the Reynolds number using equation 1, below, prompted the use of a viscous, laminar model.

$$Re = \frac{\rho v D_H}{\mu} \quad (1)$$

For the purposes of the simulations the following values were assumed: blood density (ρ) is 1060 kg/m³, dynamic viscosity (μ) of 0.0035 Pa, characteristic length scale ($D_H$) as the arterial diameter of 4 mm, and maximum velocity (v) of 0.8 m/s yielded an estimated Reynolds Number (Re) of about 1000, which is well within the laminar range. The base assumptions presented herein were used in subsequent analyses of the arteriovenous graft.

Example 2: Physical Model and Computational Mesh

A series of idealized, straight arteriovenous grafts were constructed using a commercial CAD software (DesignModeler, ANSYS, Canonsburg, Pa.) based upon the aforementioned data for typical arterial and venous presentations as described with above. In each simulation, the inner diameter of the artery was set at 4 mm and the inner diameter of the vein was set as 8 mm. An arteriovenous graft was simulated tapering from a 4 mm diameter on the arterial end to a 7 mm diameter on the venous side. These dimensions were selected for evaluation to fit both within the range of 3-5 mm for the brachial and radial arteries, and within the range of 6-10 mm for the axillary and basilic veins. The length of the arteriovenous graft was simulated at 150 mm ±2 mm, depending on the angle of attachment at the artery.

To assess the range of venous anastomosis configurations that may be utilized by a surgeon, the venous attachment described herein was simulated at various angles including 90°, 60°, 45°, 30°, 15°, and 13°. In the simulated models with the tapered 4 mm to 7 mm arteriovenous graft, the angles of attachment corresponded to semi major axis of the venous anastomoses of 7 mm, 8 mm, 10 mm, 15 mm, 25 mm, and 30 mm, respectively.

Additionally, a tailored venous anastomosis was developed, with geometry designed to constrain wall shear rates in the vein to stay within physiological ranges. The tailored venous anastomosis was constructed from two distinct features: micro-digit grooves and a lachrymiform indent, both on the distal side of the graft. The three micro-digit grooves have a width of 1.0 mm and a length of 8.8 mm. These grooves were placed to further determine if arterial blood inflow velocity can be reduced to match that of the venous blood outflow. The lachrymiform overlaid over the micro-digit grooves is 13.5 mm. This indent was placed to determine such feature could further reduce the boundary layer separation and other flow perturbations at the venous end anastomosis. These two features were tested separately, examples of which are shown in FIGS. 3A and 3B, as well as together, an example of which is shown in FIG. 3C, to determine the optimal geometry of the tailored venous graft anastomosis.

A computational mesh, as illustrated in FIG. 2, on which to estimate flow fields was generated from the above described models using ANSYS Fluent (ANSYS, Canonsburg, Pa.). Care was taken to ensure that discretization was not distorted in regions of high curvature and at edges. For each simulation, the mesh size was refined until convergence was reached, following standard procedures. An inflation mesh was set at the wall of each simulation to ensure the complexities at the boundary layer could be resolved. In the present example, the inflation created a 1 mm area of seven prism elements expanding at a rate of 1.2 at the walls of the artery, vein, and arteriovenous graft as shown in the cross-sectional view 240 of FIG. 2. The 1 mm thickness for this mesh inflation was estimated using the Blasius solution for the boundary layer thickness on a flat plate, provided as equation 2:

$$\delta \approx \frac{4.91x}{\sqrt{Re_x}} \quad (2)$$

where δ is the boundary layer thickness, x is the distance along the plate, and $Re_x$ is the Reynolds number. Convergence for the standard anastomosis models required between 200,000 and 250,000 elements (FIG. 2). The custom anastomosis required on the order of 400,000 elements to resolve the complex features implemented. The micro digits in particular required an extensively fine mesh. (FIGS. 3A-3C).

Example 3: Modeling of Blood

Blood flow was modeled as a non-Newtonian fluid following the Navier-Stokes equation, provided as equation 3, below.

$$\frac{\partial}{\partial t}(\rho v_i) + \frac{\partial}{\partial x_j}(\rho v_i v_j + p\delta_{ij} - \tau_{ij}) = 0 \quad (3)$$

in which Einstein notation was used such that $v_i$ is the velocity vector, $\tau_{ij}$ is the stress tensor, Kronecker's delta $\delta_{ij}$ functions as an identity tensor, and repeated indices imply summation. Additionally, p=trace($\tau_{ij}$) is the hydrostatic pressure. The Bird-Carreau constitutive law was used to represent the non-Newtonian, pseudo-plastic nature of blood as shown in equation 4, which is appropriate for oscillatory flow having a high Wormersley number $$\left(Wo = d\sqrt{\frac{\omega \rho}{\mu}}\right),$$

in which ω represents heart rate in radians per second, and d is the artery diameter):

$$\tau_{ij} = \dot{\gamma}_{ij} v_{eff}(De) \quad (4)$$

in which the strain rate tensor $\dot{\gamma}_{ij}$ is:

$$\dot{\gamma}_{ij} = \frac{1}{2}\left(\frac{\partial v_i}{\partial x_j} + \frac{\partial v_j}{\partial x_i}\right) \quad (5)$$

and effective viscosity changes with the Deborah number De is:

$$v_{eff}(De) = v_{inf} + (v_0 + v_{inf})(1 + (De)^2)^{\frac{n-1}{2}} \quad (6)$$

Where n is a constitutive parameter and De=$\lambda\dot{\gamma}$. Here, λ is the characteristic relaxation time of the blood, and the effective shear strain rate is $\dot{\gamma}=\sqrt{2I_2}$, in which $I_2$ is the second invariant of $\dot{\gamma}_{ij}$. The parameters with respect to the material properties of blood which were used for the calculations described in the present example are listed in Table 1, below.

TABLE 1

| | |
|---|---|
| Density (ρ), kg/m³ | 1060 |
| Viscosity at zero shear rate ($\mu_0$), Pa S | 0.0056 |
| Viscosity at infinite shear rate ($\mu_{inf}$), Pa S | 0.0035 |
| Relaxation time (λ), s | 3.313 |
| Power index, (η) | 0.3568 |

Example 4: Boundary Conditions

Figure 4A:
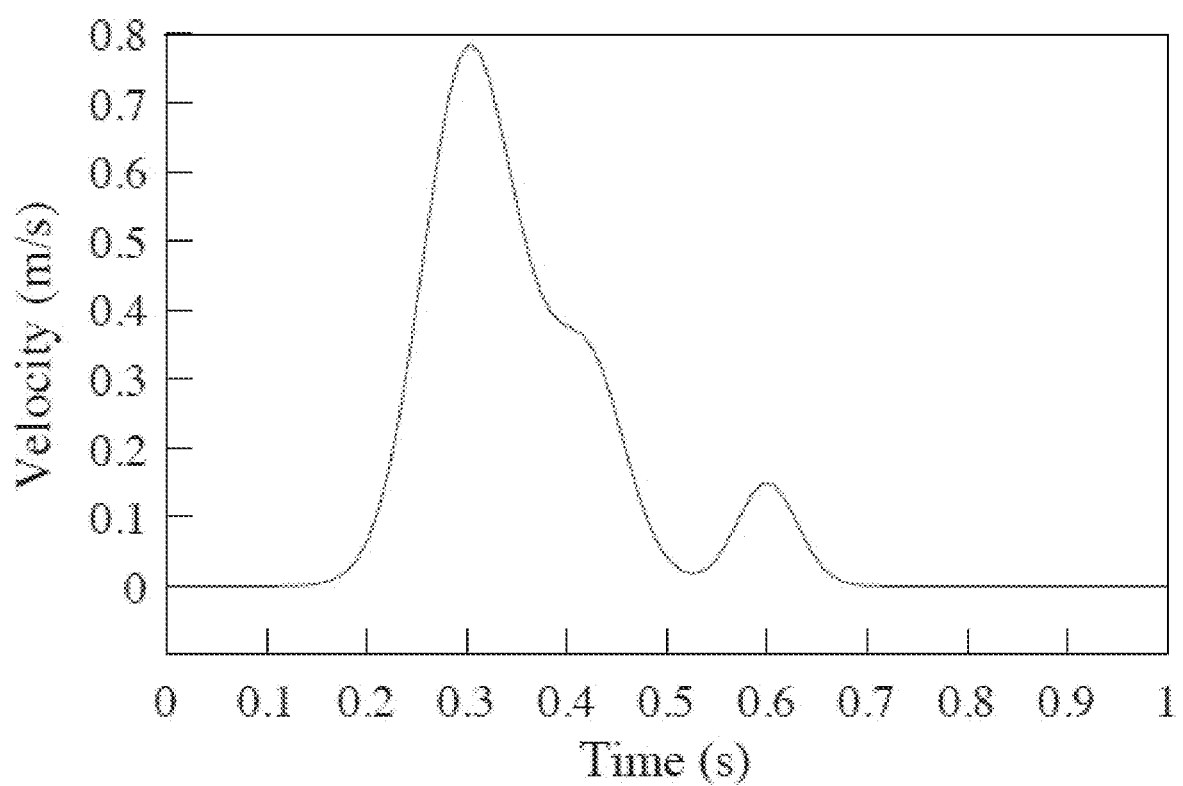
FIGS. 4A-4B show the velocity function for the arterial inlet in multiple instances.
Figure 4B:
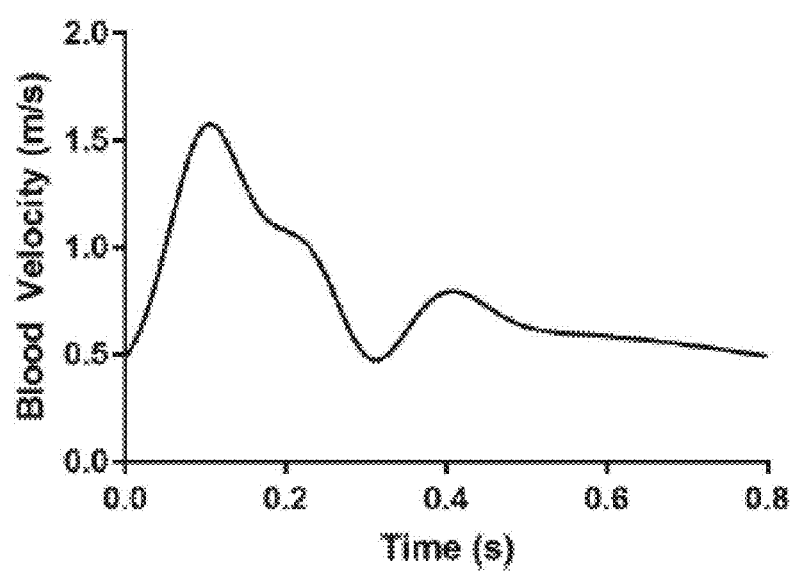

The inlet condition for the artery was based on velocity wave forms measured in the radial and brachial arteries, which were reconstructed using Gaussian wave fitting converted to a Fourier series:

$$f(t)=a_0+\Sigma_{n=1}^{\infty}\cos(\omega nt)+\Sigma_{n=1}^{\infty} b_n \sin(\omega nt) \quad (7)$$

Where $a_n$ and $b_n$ are curve fit parameters, t is the simulation time, and ω is angular frequency. Adjusting this allows effective control of simulated heart rate. Fitting was performed using MATLAB (The Mathworks, Natick, Mass.) using eight terms. Exemplary velocity functions which can be used to represent the arterial inlet velocity throughout the simulations are provided in FIGS. 4A and 4B.

For example, the volumetric flow rate into the arteriovenous graft was measured in the simulations to be 700 ml/min, which is within the range of healthy flow rate for an arteriovenous graft. The venous system does not experience significant pulsatile flow. During the simulations, the flow from the distal side of the vein to the proximal side of the vein was specified to be a constant. The vein inlet condition we set at a constant velocity of 15 cm/s, as appropriate for flow in the axillary vein.

Outlet boundary conditions are a well-known challenge for vascular flow. Although standard practice used in pipe flow calculations is to use pressure outlet conditions, this fails to account for the downstream effects that are present in the circulatory system. A common approach is therefore to use an outflow boundary condition for simulating vascular systems, especially for arteriovenous grafts. Following National Kidney Foundation KDOQI Clinical Practices, the inflow of the simulations was distributed so that 90% was sent to the graft and 10% went to the distal artery. The vein outflow simulation was further distributed from the graft so that 85% of the inflow went to the proximal vein and 15% to the distal vein.

Additionally, no-slip boundary conditions were used along the vessel walls, and vessels were treated as rigid.

Example 5: Solution Procedure

Each of the above equations were solved using the ANSYS Fluent CFD solver (ANSYS, Canonsburg, Pa.). In the calculations, a semi-implicit method for pressure-linked equations ("SIMPLE") pressure-velocity coupling method was used with second order spatial discretization and first order transient discretization. A pressure-implicit with splitting-operations ("PISO") method was also used, with second order spatial discretization and transient discretization, with negligible difference in results but with increased computation time.

Hybrid initialization was done by solving Laplace's equation, $\nabla^2\varphi=0$, in which φ is a potential function defining the velocity field: v=∇φ. The boundary conditions which were used in the hybrid initialization for the walls, inlets, and outlets of the system are as shown in equations 8-10, below.

$$\left.\frac{\partial \varphi}{\partial n}\right|_{wall} = 0 \quad (8)$$

$$\left.\frac{\partial \varphi}{\partial n}\right|_{inlet} = v_\perp \quad (9)$$

$$\varphi_{outlet} = 0 \quad (10)$$

In a first example, convergence for the transient calculation was achieved with a time step of 0.01 s for 100 time steps, which enabled simulation of one pulse with high accuracy. In a second example, convergence was achieved with a time step of 0.0025 s for 320 time steps. In both examples, twenty iterations or fewer were required at each time step, as is common practice. Convergence criteria for the continuity, x-velocity, y-velocity, and z-velocity were all set at an absolute tolerance of 0.001. Each venous-end anastomosis angle was simulated three times using three different messes having the same number of elements. For each of the examples, the results were averaged to remove any error which could develop from meshing where minimized.

Example 6: Shear Strain Rates with Varying Anastomosis Angle

Figure 5A:
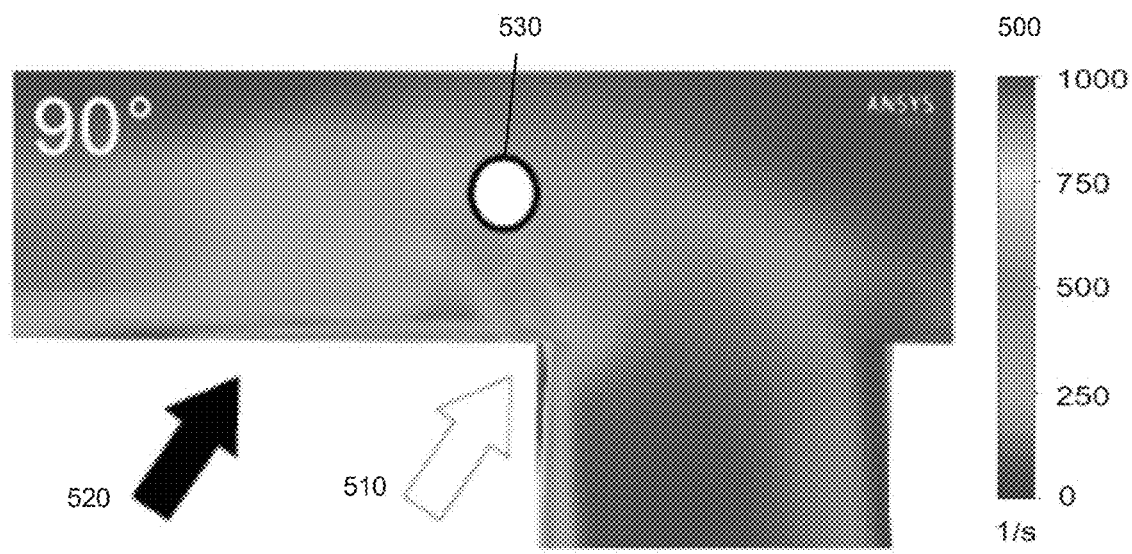
FIGS. 5A-5F show cross sectional views of the various venous anastomoses showing the blood shear strain rate fields 30% of the way through the cardiac cycle. Anastomoses with insertion angles of (FIG. 5A) 90°, (FIG. 5B) 60°, (FIG. 5C) 45°, (FIG. 5D) 30°, (FIG. 5E) 15°, and (FIG. 5F) 13°. White arrows indicate locations of peak shear strain rates on the wall; black arrows indicate locations of flow separations.
Figure 5B:
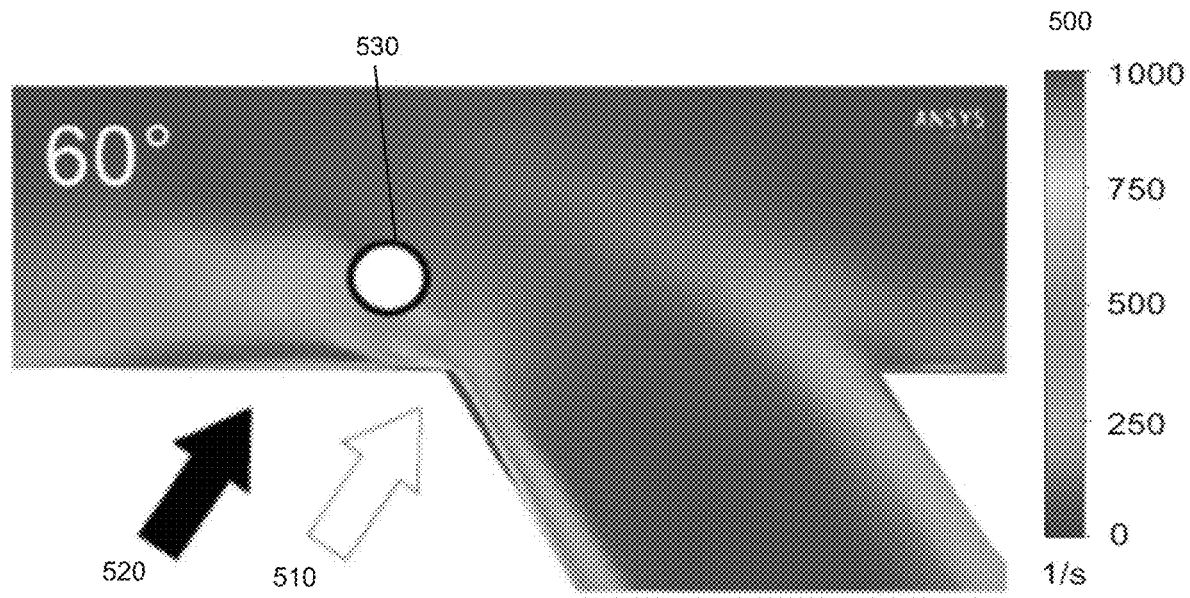
Figure 5C:
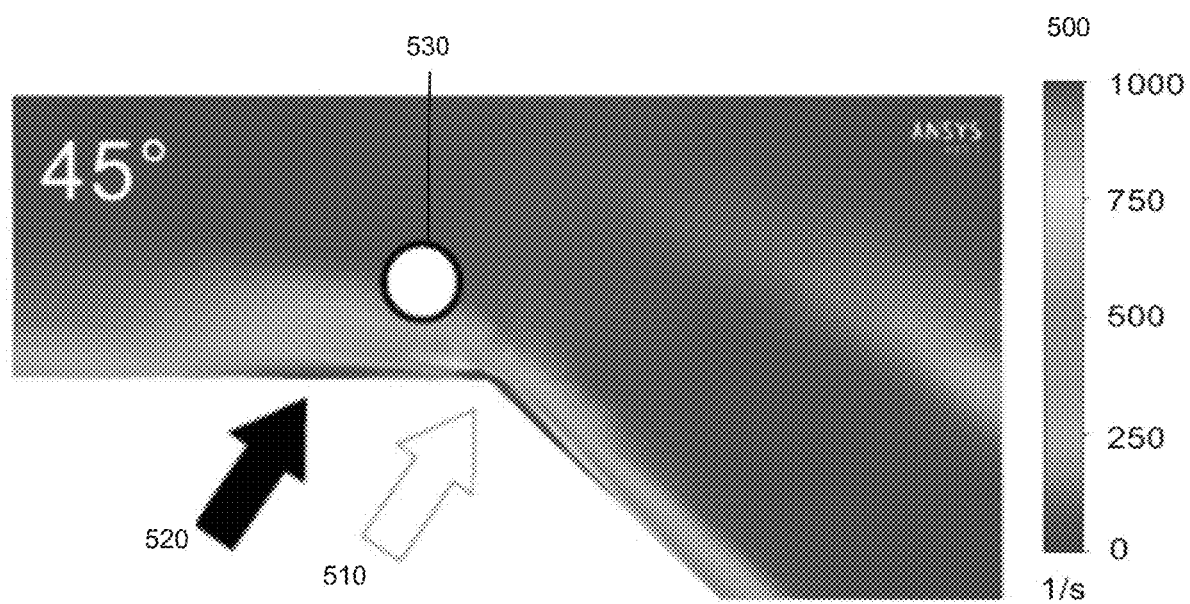
Figure 5D:
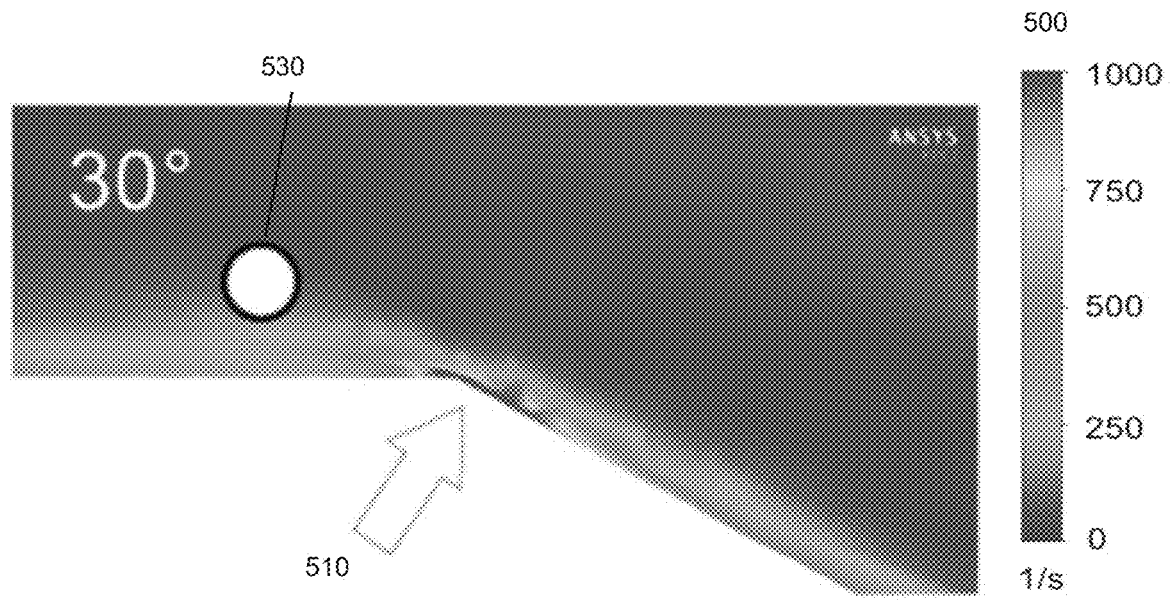
Figure 5E:
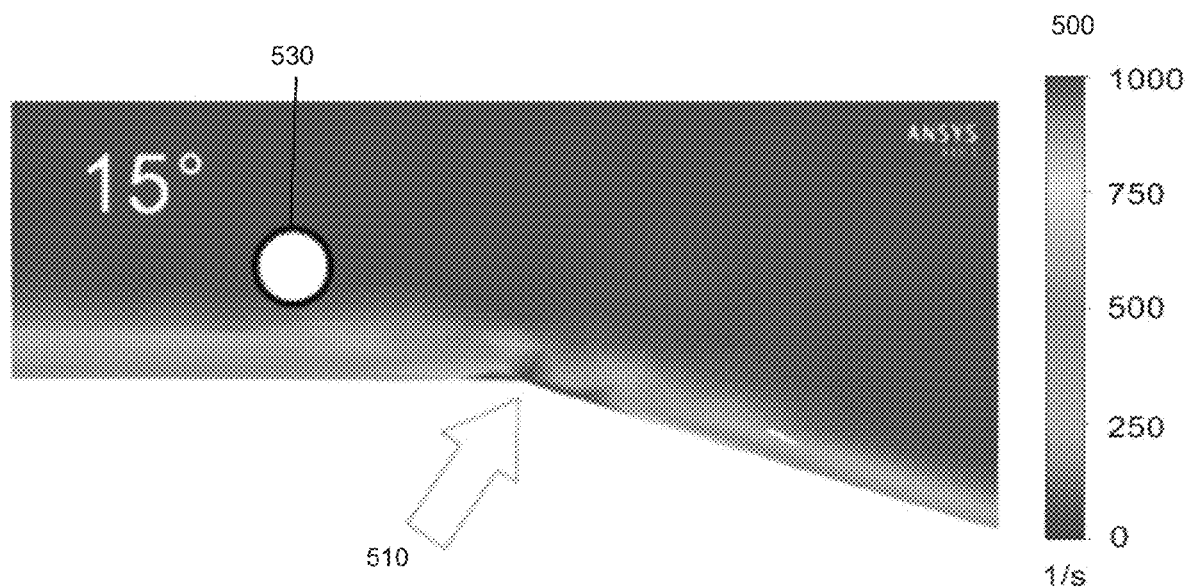
Figure 5F:
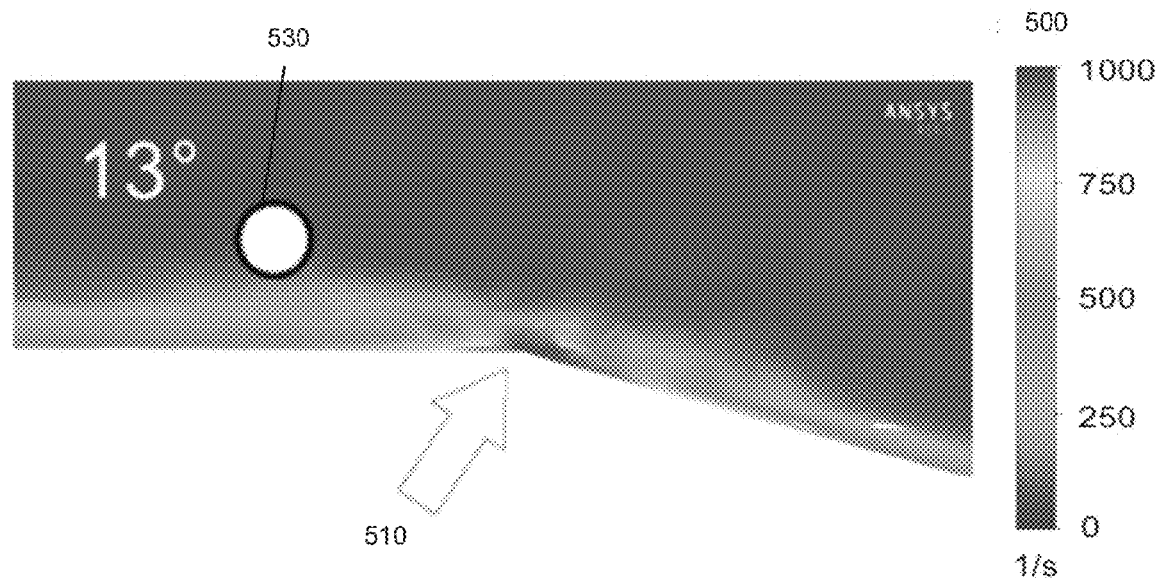

Blood flow entering the axillary vein from a brachio-axillary arteriovenous graft leads to perturbations of the venous blood flow. To determine the location and extent of perturbations, flow fields were plotted over cross sections of the anastomoses at the peak of wall shear strain rate. Such cross sections showed that perturbations varies with anastomosis angle θ, as shown with respect to FIGS. 5A-5F. The flow fields of FIGS. 5A-5F illustrate the flow at 0.3 seconds into the 1-second heartbeat. Specifically, FIG. 5A illustrates a flow field corresponding to an anastomoses having an insertion angle of 90°, FIG. 5B illustrates a flow field corresponding to an anastomoses insertion angle of 60°, FIG. 5C illustrates a flow field corresponding to an anastomoses insertion angle of 45°, FIG. 5D illustrates a flow field corresponding to an anastomoses insertion angle of 30°, FIG. 5E illustrates a flow field corresponding to an anastomoses insertion angle of 15°, and FIG. 5F illustrates a flow field corresponding to an anastomoses angle insertion angle of 13°.

The perturbations varied along with the anastomosis insertion angle, as evident from FIGS. 5A-5F. Each of the simulated angle anastomoses experienced a high level of shear strain rate at the distal vein connection. The shear rate is indicated via color-coding in accordance with the shear rate key 500 provided, wherein, areas indicated in red show the greatest shear rate. Such areas of high shear are indicated by white arrows 510 in each of FIGS. 5A-5F. The incidence of pathologically high shear strain rate decreased with decreasing venous anastomosis angle θ. Pathologically low shear strain rate was present in every angle anastomosis, and in severe acute angles, flow separation occurred, in which the boundary stagnates to a speed sufficiently slow that blood flow becomes pro-thrombogenic, areas of dark blue as indicated by black arrows 520 in FIGS. 5A, 5B, and 5C. The incidence of pathologically low shear strain rate decreased as anastomosis angle decreased down to 30°, then began to increase again. Additional flow disturbances, including eddies and vortices, were present in the blood flow entering the vein from the graft. These disturbances, indicated by white circles 530 in FIGS. 5A-5F improved as the anastomosis angle decreased from 90° to 30°, after which the improvements leveled out.

Figure 6A:
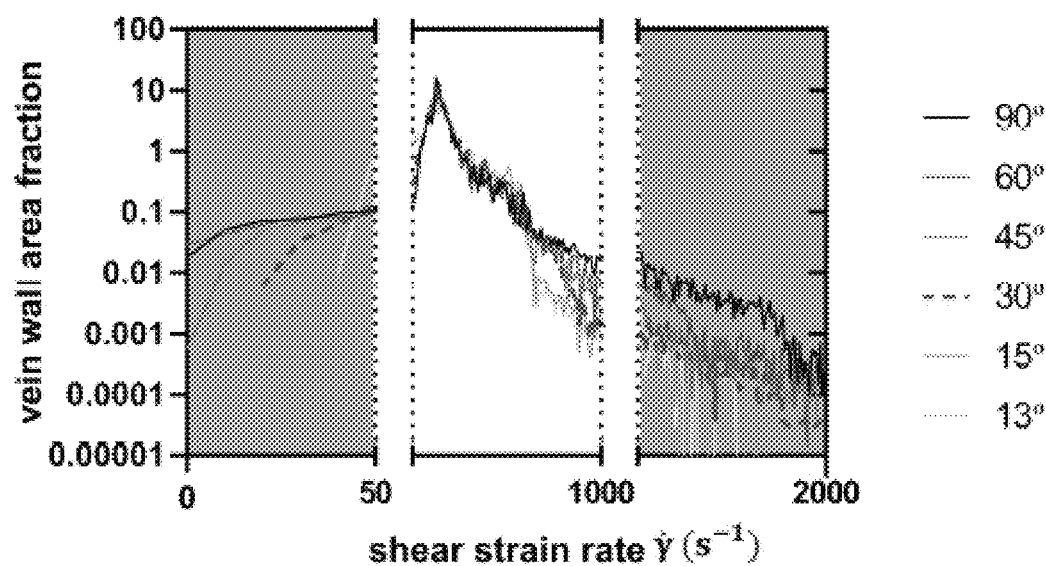
FIGS. 6A-6D show the percentage of the vein wall at each value of shear rate from 0-2000 $s^{-1}$.

To quantify the degree to which blood flow was perturbed pathologically over one heart cycle, the shear strain rate was recorded at each of the mesh cells on the vein wall for each time point, normalized with respect to area, and visualized on a histogram. The results of the quantification are provided in the graph illustrated in FIG. 6A. The normalized distributions revealed an important role for the venous end graft anastomosis angle in determining the fraction of the vein wall that experienced pathological shear strain rates. The logarithmic representation of area fraction in FIG. 6A demonstrates that the physiological range increased as the venous anastomosis angle increased, and the small fraction of blood flow that was outside of the physiological range increased as the venous anastomosis insertion angle increased to 90°.

Figure 6B:
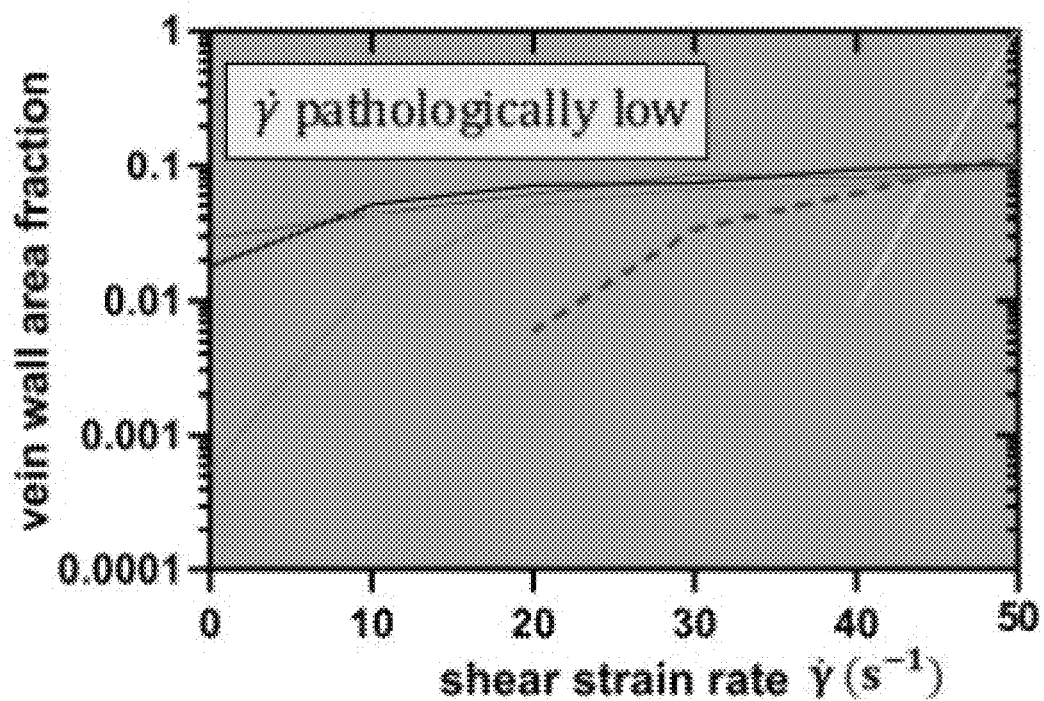
Figure 6C:
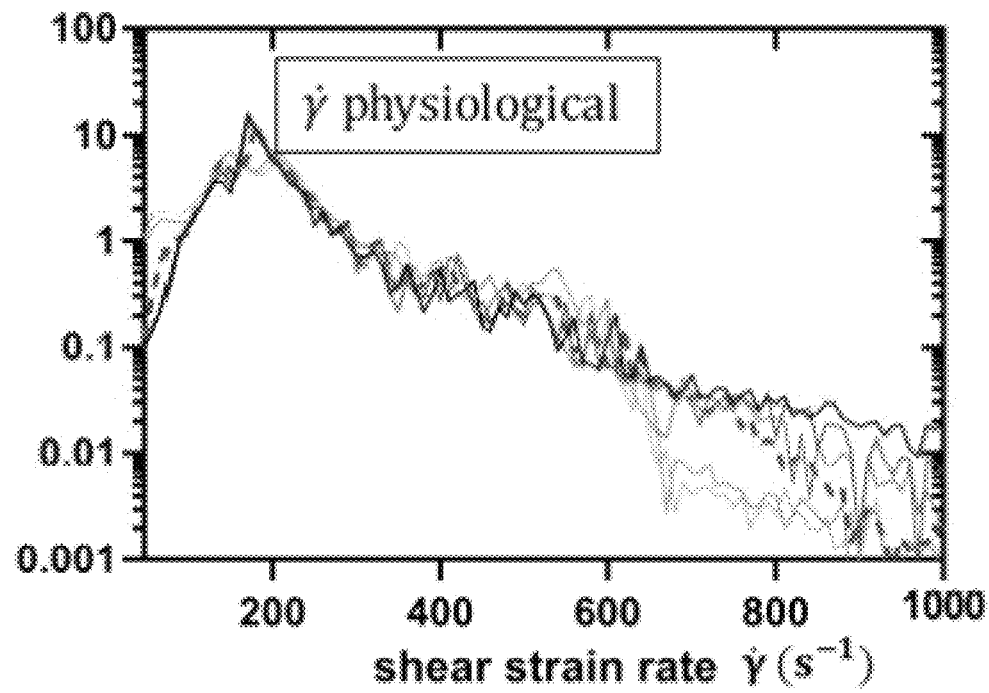
Figure 6D:
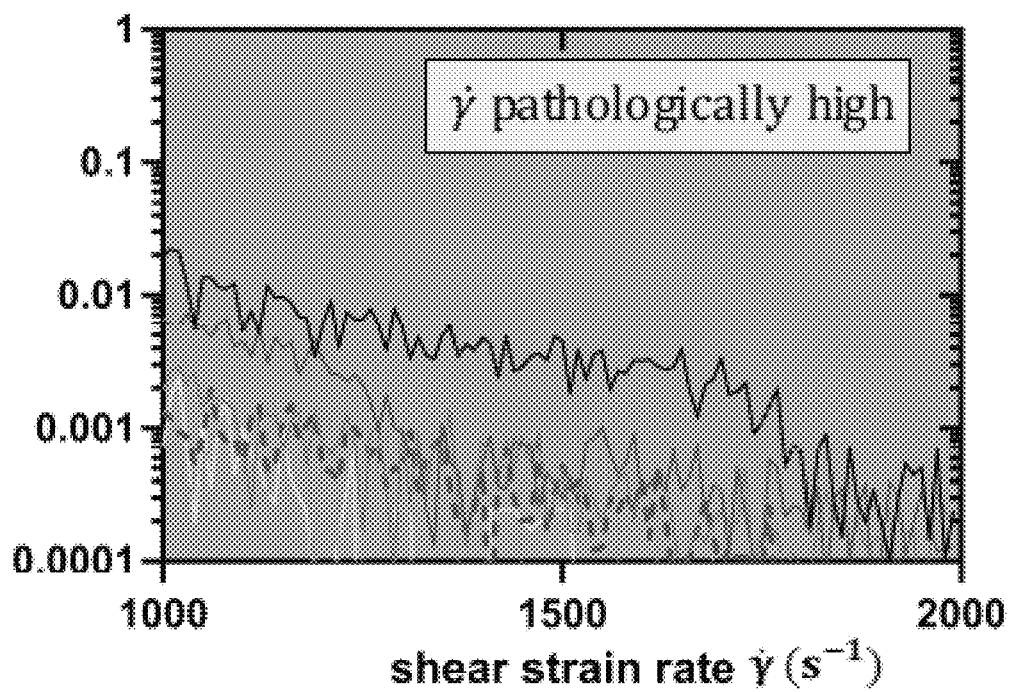

Segments of the histogram were magnified to evaluate regions of shear strain rates. Specifically, FIG. B illustrates a histogram of the pathologically low (0-50 s$^{-1}$) shear strain rates, FIG. 6C illustrates a histogram of the physiological (50-1000 s$^{-1}$) shear rates, and FIG. 6D illustrates a histogram of the pathologically high (1000-2000 s$^{-1}$) shear strain rates. In the pathologically low histogram of FIG. 6B, the shear strain rates are shown to decrease as the anastomosis angle drops from 90° to 30°, but increased slightly for the more acute angles. In the high shear strain rate histogram of FIG. 6D, the area fraction is shown to have dropped as the venous anastomosis angle was decreased.

The prevalence of pathologically low and high shear strain rate, as well as the eddies and vortices created by the blood flow entering the vein from the graft, show that there was a need for further optimization beyond changing the anastomosis insertion angle. Even at the optimal angle of 30° perturbations were still present in the flow which can lead to unhealthy high and low shear strain rate and additional flow disturbances.

Example 7: Optimization of Graft Geometry

Figure 7A:
FIGS. 7A-7C show cross sectional view of the various venous anastomoses showing the blood shear strain rate fields 30% of the way through the cardiac cycle.
Figure 7B:
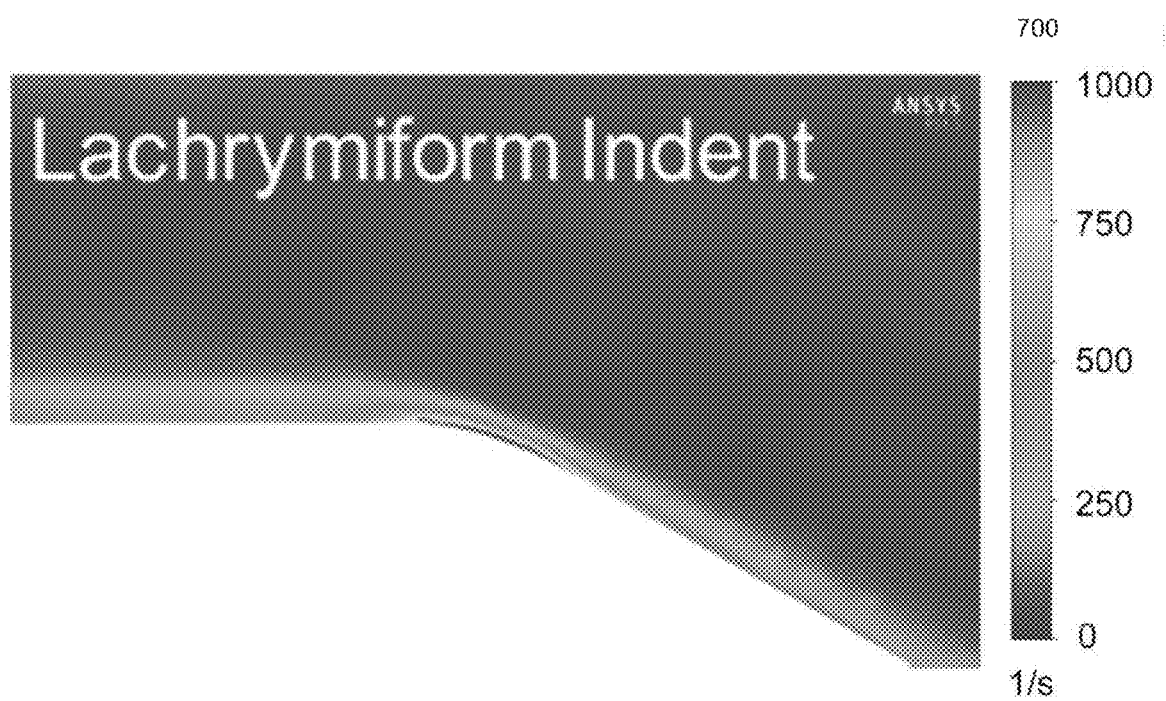
Figure 7C:

Additional simulations were performed to determine an optimized graft geometry for a venous anastomosis having a 30° insertion angle. Cross-sectional views of the venous anastomoses showing the blood shear strain rate are provided in FIGS. 7A-7C. For example, in a first simulation, a plurality of micro-grooves, such as those illustrated with respect to FIG. 3A, were incorporated in attempt to decrease the velocity of the incoming blood flow and align the flow direction to more closely match that of the venous blood flow. This adaptation provided a significant reduction in pathologically high and low shear strain rate, no flow separation, and reduced vorticity was observed during the simulation, as shown in FIG. 7A. In a second simulation, a lachrymiform indent, as illustrated with respect to FIG. 3B, was incorporated on the graft. Including the indent in the graft also showed an improvement in the shear strain environment of the blood flow and a decrease in flow perturbation, as shown in FIG. 7B. A third simulation was performed including both a plurality of grooves and indent in the graft geometry, as shown in FIG. 3C. This simulation provided the greatest reduction in unhealthy high and low shear strain rate, eddies, and vorticities, as indicated in FIG. 7C. The cross-sectional views of FIGS. 7A-7C represent measurements taken at 0.3 seconds into the 1 second heart beat where the shear strain rate was at its peak. As described above, the color-coded key 700 provides information relating to the shear rate experienced at various points throughout the venous anastomoses.

Figure 8A:
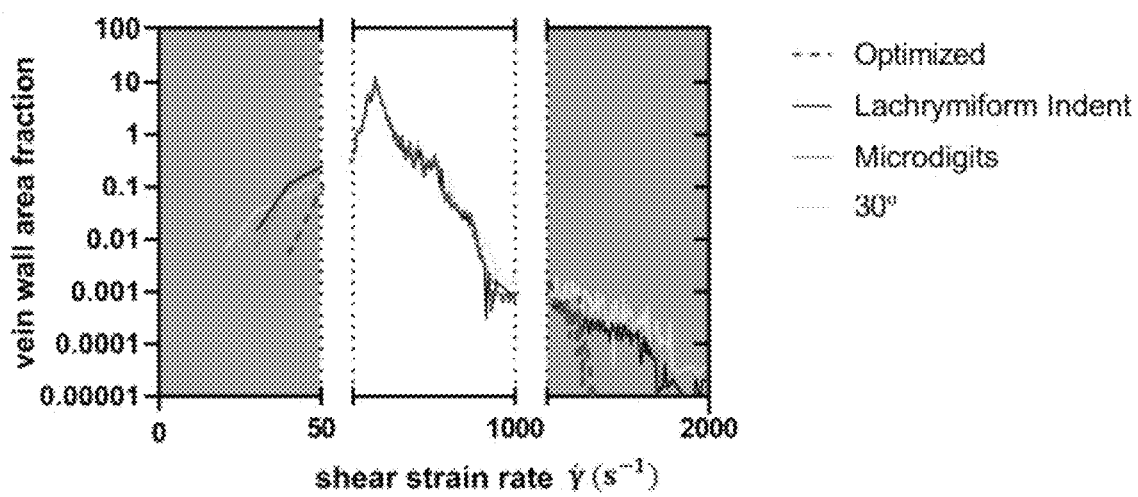
FIGS. 8A-8D show the percent of the vein wall at each value of shear strain rate from 0-2000 $s^{-1}$. The three iterations of the tailored venous anastomosis and the 30° simple anastomosis are shown.
Figure 8B:
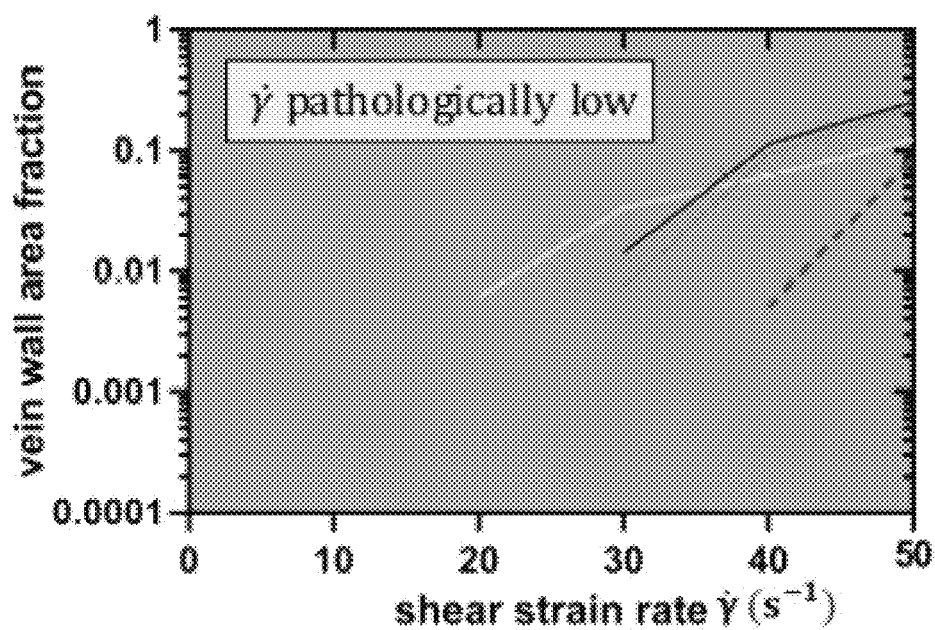
Figure 8C:
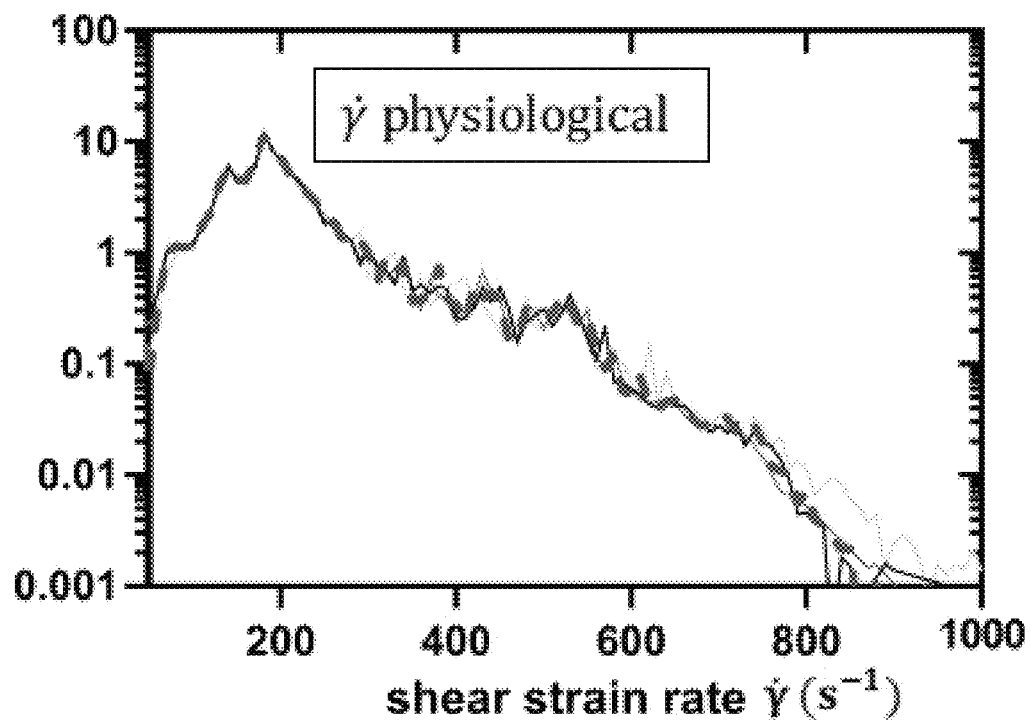
Figure 8D:
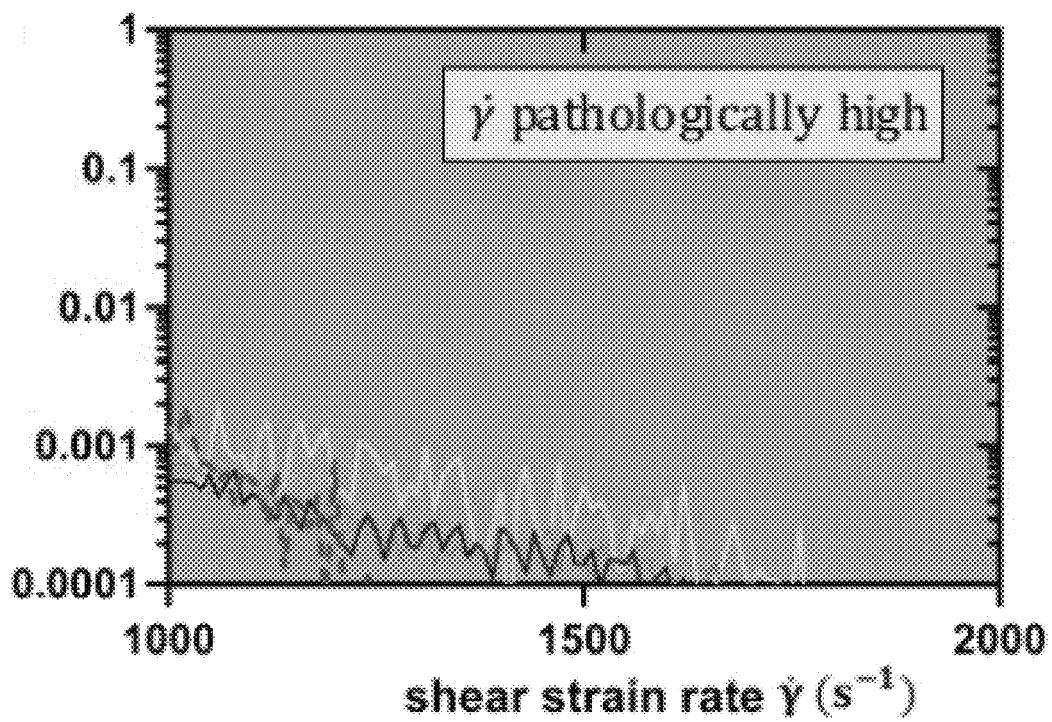

Again, to better quantify the improvements described in the iterations of the tailored anastomosis, the shear strain rate for each configuration was recorded and plotted on a three part histogram, provided in FIG. 8A. Due to the superior performance in the above analysis, data relating to a 30° simple anastomosis was included in the histogram as well as a reference point for comparison. Each iteration of the tailored anastomosis provided a healthier distribution of shear strain rate as compared to the 30° simple venous anastomosis. Similar to above, FIGS. 8B-8D illustrate enlarged views of various portions of the histogram of FIG. 8A. Specifically, FIG. 8B illustrates an enlarged view of the pathologically low shear strain rate range within the vein wall, FIG. 8C illustrates an enlarged view of the physiologically healthy range of wall shear rate within the vein, and FIG. 8D illustrates an enlarged view of the pathologically high shear strain rate within the vein wall. As shown in FIGS. 8B-D, there is a clear reduction in the pathological shear strain values. Furthermore, the combination of the two features, indicated in the histograms of FIGS. 8A-8D as a dashed red line, had an even greater improvement compared to each individual feature.

Figure 9:
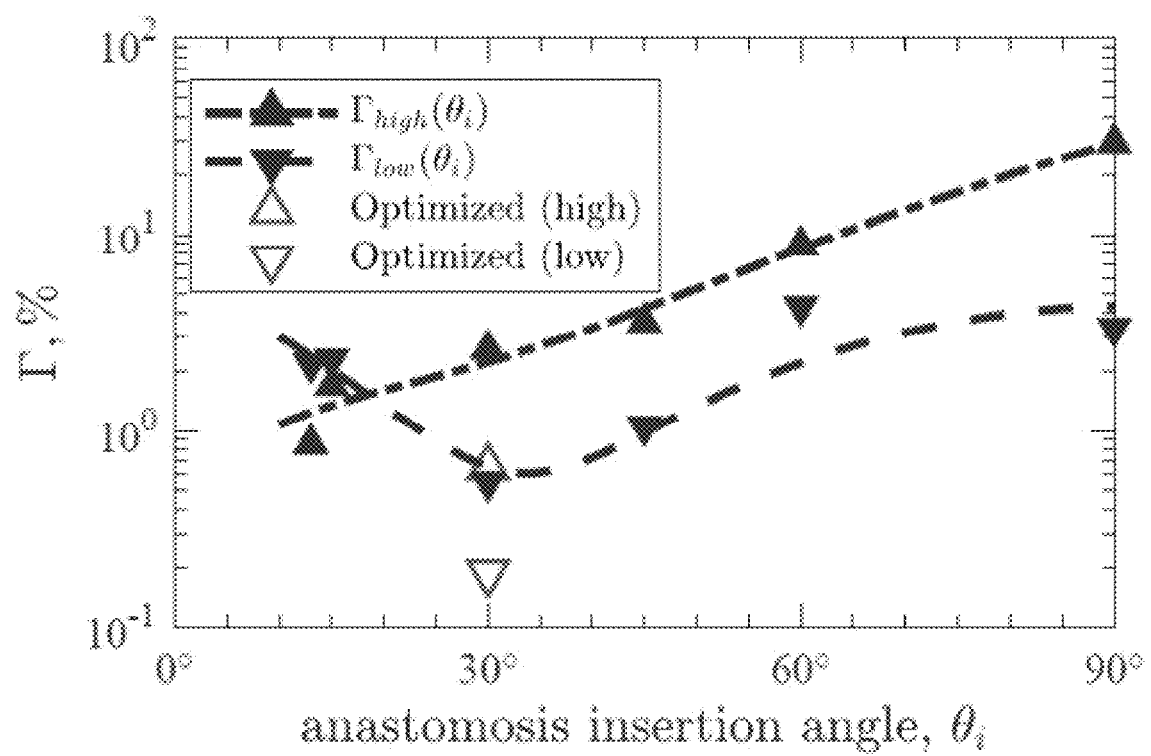
FIG. 9 is a graph showing the degree to which differing anastomosis designs induced pathologically high (represented by increasing $\lceil_{high}$) and pathologically low (represented by increasing $\lceil_{low}$) shear strain rates at the vein wall. These summary metrics suggested that the fraction of vein wall area undergoing pathologically high shear strain rates diminished with decreasing anastomosis insertion angle, while that undergoing pathologically low shear strain rates reached a minimum for an insertion angle near 30°. The severity of the pathological shear strain rates was reduced substantially by shape optimization (open triangles).

In order to quantify these trends succinctly, two metrics were defined to quantify the degree to which each venous anastomosis disrupted flow pathologically. For shear strain rates in the 50 histogram bins of the pathologically low range, $\Gamma_{low}$ was defined as the sum of a term that was the product of the inverse of the shear strain for a bin ($1/\dot{\gamma}_n$) and the area fraction $\varnothing_n$ for that bin:

$$\Gamma_{low} = (100\%)\dot{\gamma}_{min}\sum_{n=1}^{50}\frac{\varnothing_n}{\dot{\gamma}_n} \quad (11)$$

where the normalization of $\dot{\gamma}_{min}=1\ s^{-1}$ represented the lowest shear strain rate of the series. For shear strain rates in the 1001 histogram bins of the pathologically high range, $\Gamma_{high}$ was defined as the sum of a term that was the product of the shear strain for a bin ($\dot{\gamma}_n$) and the area fraction $\varnothing_n$ for that bin:

$$\Gamma_{high} = \frac{100\%}{\dot{\gamma}_{max}}\sum_{n=1000}^{2000}\varnothing_n\dot{\gamma}_n \quad (12)$$

where the normalization of $\dot{\gamma}_{max}=2000\ s^{-1}$ represented the highest shear strain rate of the series. The summary metrics are provided in FIG. 9, illustrating the degree to which differing anastomosis designs induced pathologically high (represented by increasing $\Gamma_{high}$) and pathologically low (represented by increasing $\Gamma_{low}$) shear rates at the vein wall. The summary metrics suggested that the fraction of the vein wall area undergoing pathologically high shear strain rates diminished with the decreasing the anastomosis insertion angle, while that undergoing pathologically low shear strain rates reached a minimum for an insertion angle near 30°. These metrics were minimized in an optimization that altered the shape of the graft near the anastomosis. The results showed that modification of the shape of the graft could be used to reduce the fraction of the vein wall that experienced pathological shear strain rates, as indicated with open triangles in the graph of FIG. 9.

Example 8: Shear Rate Optimization of the Venous-End Anastomosis of an Arteriovenous Graft The analysis of standard venous anastomoses indicated that standard graft design cannot introduce arterial blood into the venous system without creating areas of excessively low and excessively high wall shear rate. As such, an optimized anastomosis, as illustrated in FIGS. 3A-3C, was studied. For this design, an intact boundary layer was maintained (as shown in FIG. 7A). The data corresponding to the simulations is provided in FIGS. 6A-6D, 8A-8D, and 9; the data suggests that the optimized anastomosis reduced instances of shear rate outside the physiological range.

Using ANSYS Fluent computational fluid dynamics package as described above an arteriovenous graft system was modeled and simulated with pulsatile blood flow. The system consisted of a tapered graft connecting an artery and vein. Venous anastomoses were simulated at various insertion angles including 90°, 60°, 45°, 30°, 15°, and 13°. Additionally, various novel graft designs including micro-digit imprints were tested. Potential for thrombosis was measured as the area of the vein wall experiencing unhealthy shear rates (shear rates <50 1/s and >1000 1/s).

Figure 10:
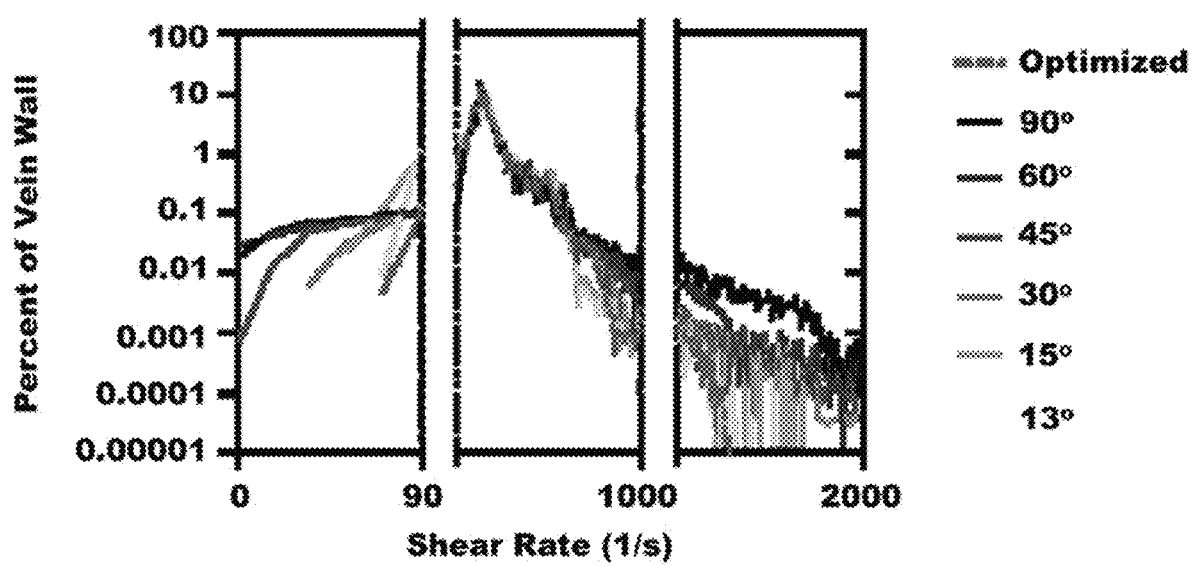
FIG. 10 shows the percentage of the vein wall at each value of shear rate from 0-2000 $s^{-1}$ for the tailored arteriovenous graft with an angle of attachment of 30° shown in FIG. 3C compared to six different non-tailored venous anastomosis angles.

As stated above, a 90° anastomosis lead to the largest flow disruption and incidence of unhealthy high and low shear rate on the vein wall. Decreasing the anastomosis angle provided an improvement on the shear environment. Compared to the 90° anastomosis, a 13° anastomosis had the largest decrease in unhealthy high shear rate (by 97%; P<0.0001), and 30° anastomosis had the largest decrease in unhealthy low shear rate (by 94%; P<0.05). The graft design illustrated in FIG. 3C, including a plurality of micro-grooves and an indent, further reduced the high and low shear rates (P<0.0001 and P<0.05, respectively) as indicated in the graph provided in FIG. 10.

Decreased arteriovenous graft venous anastomosis angle can dramatically improve the shear environment. Optimized geometry of the graft can further normalize the shear rates, and may decrease the incidence of stenosis at the venous-end anastomosis.

Example 9: Shear Strain Rates with Varying Anastomosis Angle Over the Course of a Heartbeat As described above, blood flow entering the axillary vein from a brachio-axillary arteriovenous graft leads to perturbations of the venous blood flow. In order to quantify the degree to which blood flow was pathologically perturbed over one heart cycle, the shear rate was recorded at each of the mesh cells on the vein wall for each time point. The corresponding data is provided on the color-coded maps shown in FIGS. 11A-11F, which shows the distribution of shear rate during one heartbeat. As shown in FIGS. 11A-11F, the venous-end anastomosis angle is critical in determining the fraction of the vein wall that experiences pathological shear rates.

Figure 11A:
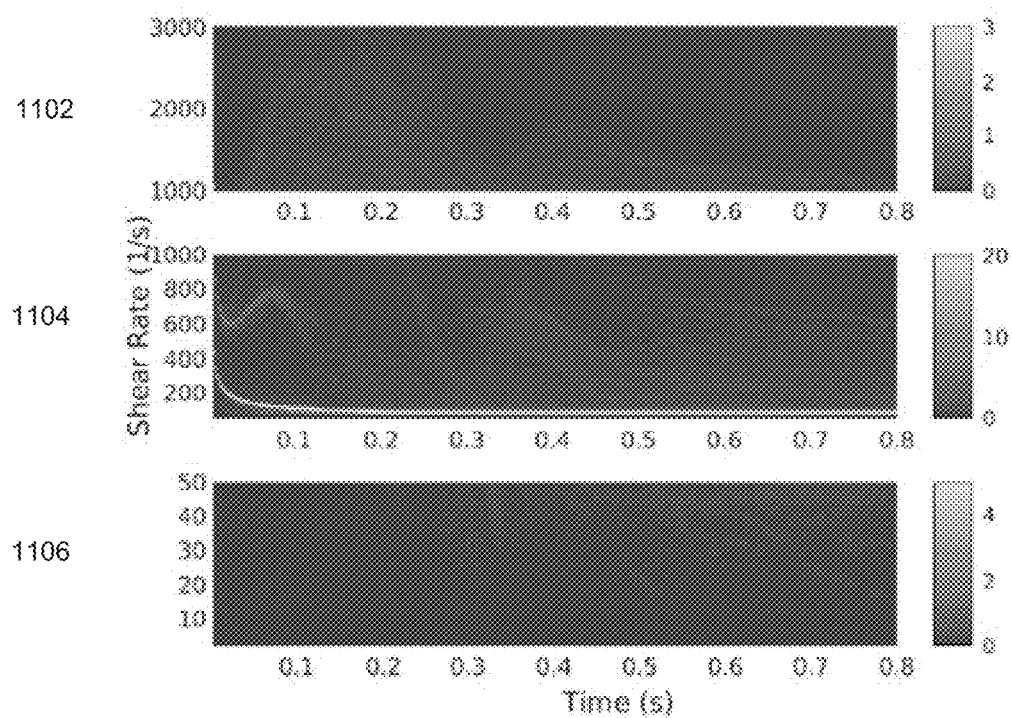
FIGS. 11A-11F show the percentage of the vein wall experiencing physiological and pathological shear rates over the course of one heartbeat. Each figure includes three graphs indicating pathologically low wall shear rates (0-50 $s^{-1}$), physiological wall shear rate (50-1000 $s^{-1}$), and pathologically high wall shear rate (1000-3000 $s^{-1}$). Anastomoses with insertion angles of (FIG. 11A) 90°, (FIG. 11B) 60°, (FIG. 11C) 45°, (FIG. 11D) 30°, (FIG. 11E) 15°, and (FIG. 11F) 13°.
Figure 11B:
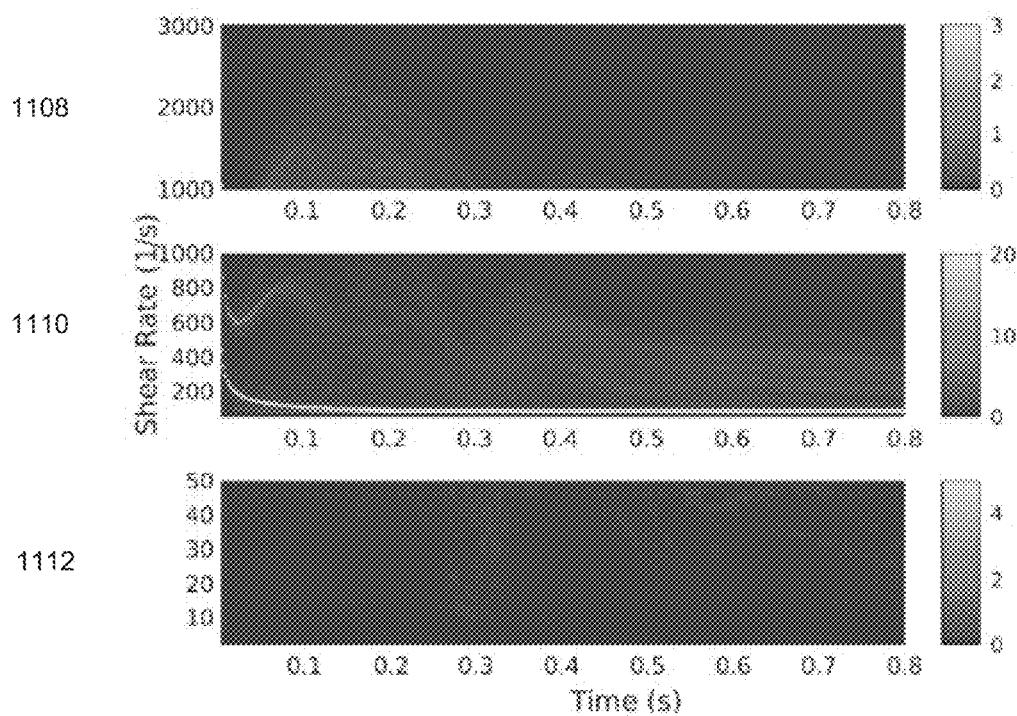
Figure 11C:
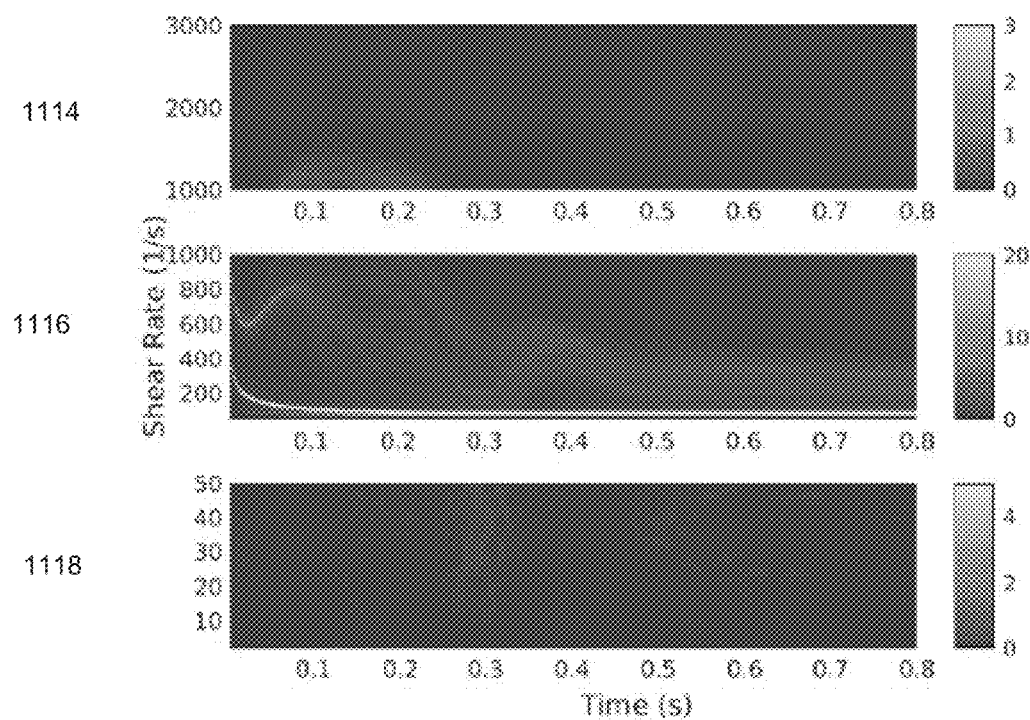
Figure 11D:
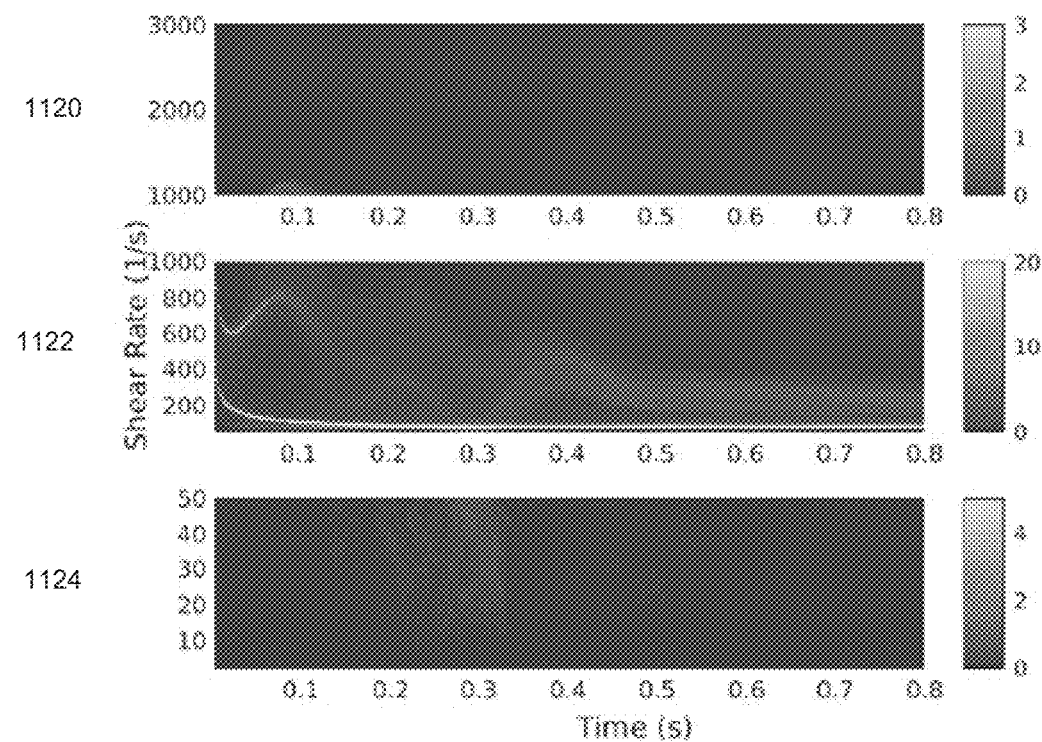
Figure 11E:
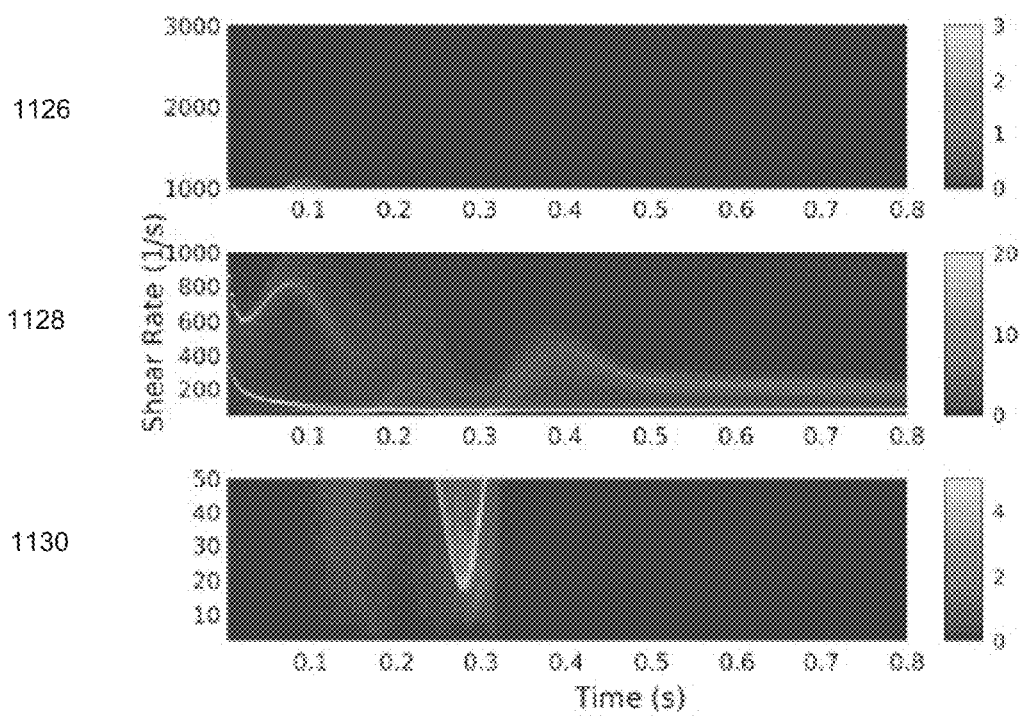
Figure 11F:
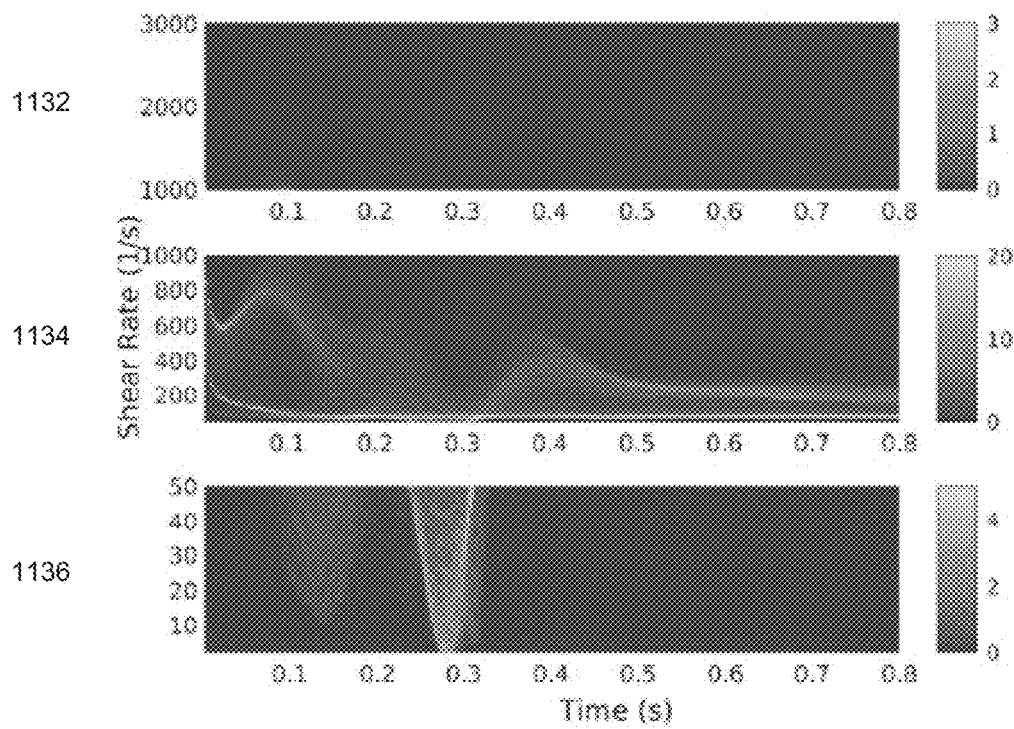

Specifically, the graphs provided in FIGS. 11A-11F illustrate the percentage of the vein wall which experiences physiological and pathological shear rates over the course of one heartbeat, for a range of anastomosis angles. FIG. 11A illustrates the physiological and pathological values associated with an anastomosis angle of 90°, FIG. 11B illustrates the physiological and pathological values associated with an anastomosis angle of 60°, FIG. 11C illustrates the physiological and pathological values associated with an anastomosis angle of 45°, FIG. 11D illustrates the physiological and pathological values associated with an anastomosis angle of 30°, FIG. 11E illustrates the physiological and pathological values associated with an anastomosis angle of 15°, and FIG. 11F illustrates the physiological and pathological values associated with an anastomosis angle of 13°. Each of the graphs of FIGS. 11A-11F are divided into three sections, graphs illustrating pathologically low wall shear rates (0-50 s$^{-1}$) 1102, 1108, 1114, 1120, 1126, 1132; graphs illustrating physiological wall shear rates (50-1000 s$^{-1}$) 1104, 1110, 1116, 1122, 1128, 1134; and graphs illustrating pathologically high wall shear rate (1000-3000 s$^{-1}$) 1106, 1112, 1118, 1124, 1130, 1136.

Similar to those described above, the graphs of FIGS. 11A-11F are provided in color-coded maps. As shown, the simulations demonstrated that the venous-end anastomosis angle has a significant effect on the shear environment of the adjacent vein wall. For example, the simulation including an anastomosis angle of 90°, illustrated in FIG. 11A, indicated that most of the pathological flow fields were in the high shear rate range early in the heart cycle. On the contrary, the simulation including an anastomosis angle of 13°, illustrated in FIG. 11F, indicated very few regions of high shear rates in the early stages of the heart cycle, but showed pathologically low shear rates evident in the middle of the heart cycle. As shown, the anastomosis angle can clearly have varying impacts on the pathological shear rates at different times throughout the heart cycle.

Figure 12A:
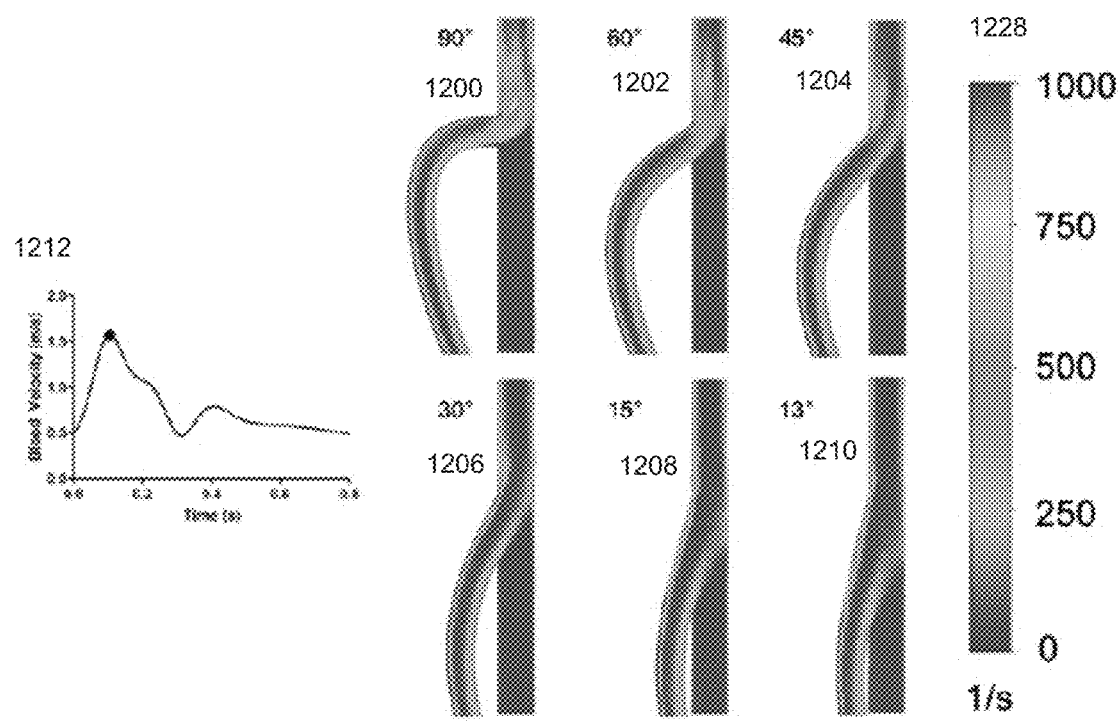
FIGS. 12A-12B show cross-sections of anastomoses at selected times over the course of a heartbeat.
Figure 12B:
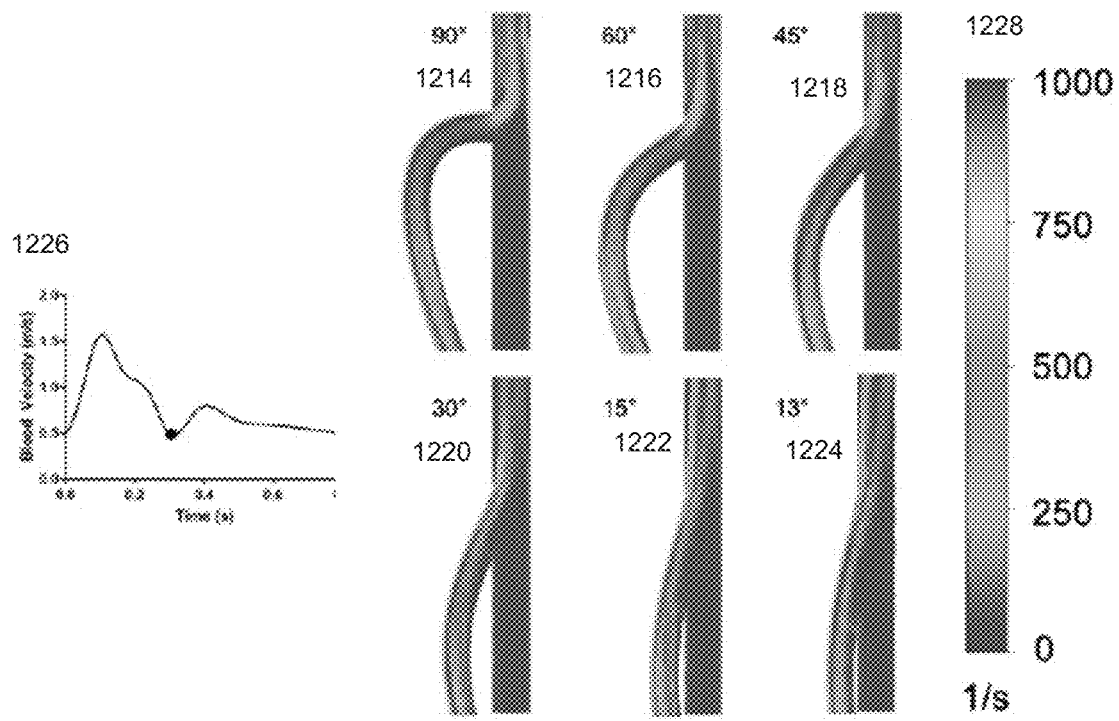

Example 10: Effect of Varying Anastomosis Angle on Shear Environment Over the Course of a Heartbeat Flow fields corresponding to the simulations were plotted over cross-sections of the anastomoses at the peak of high and low wall shear rates in order to further understand how the shear environment was affected. Such images are provided as FIGS. 12A and 12B. Specifically, cross-section views of the peak of high wall shear rate is provided at 0.1 seconds into a 0.8 second heartbeat are illustrated for various anastomoses angles 1200, 1202, 1204, 1206, 1208, 1210 in FIG. 12A. A graph 1212 representing the peak high wall shear rates throughout the heartbeat is provided. The corresponding peak of low wall shear rates are provided at 0.1 second intervals into the 0.8 second heartbeat for various anastomoses angles 1214, 1216, 1218, 1220, 1222, 1224 are shown in FIG. 12B. Similarly, a graph 1226 indicating the point of peak low wall shear rates is provided.

At the peak of high shear rate, 0.1 seconds into the heartbeat, high wall shear rate was determined to be localized to the distal end of the anastomosis and to the opposite vein wall. The high shear rates are indicated in red, as shown in the shear rate color-coded key 1228 provided in FIGS. 12A and 12B. The incidence of the high shear rate decreased along with the venous-end anastomosis angle. At the peak of low shear rate, 0.3 seconds into the heartbeat, low wall shear rates were found to be localized on the vein wall just distal to the anastomosis and opposite to the anastomosis. As such, the simulations show that high and low shear rates can impact different anatomical regions along the graft-to-vein anastomosis.

Figure 13A:
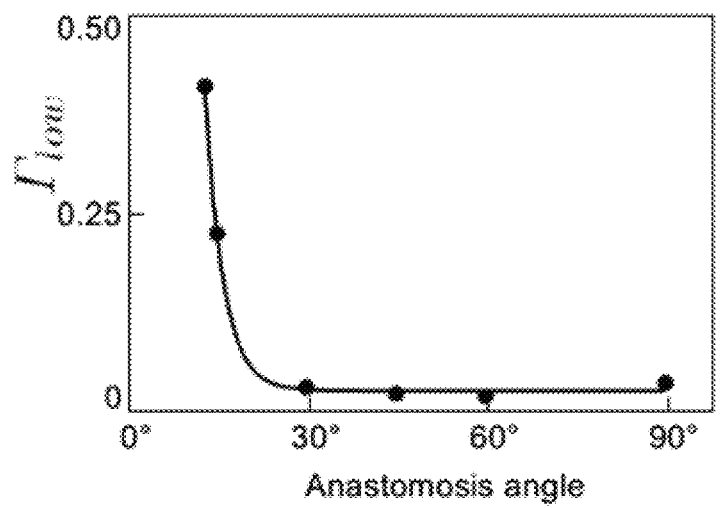
FIGS. 13A-13B show summary metrics showing the degree to which differing anastomosis designs included pathologically low shear strain rates at the vein wall (FIG. 13A) and pathologically low shear strain rates at the vein wall (FIG. 13B).
Figure 13B:
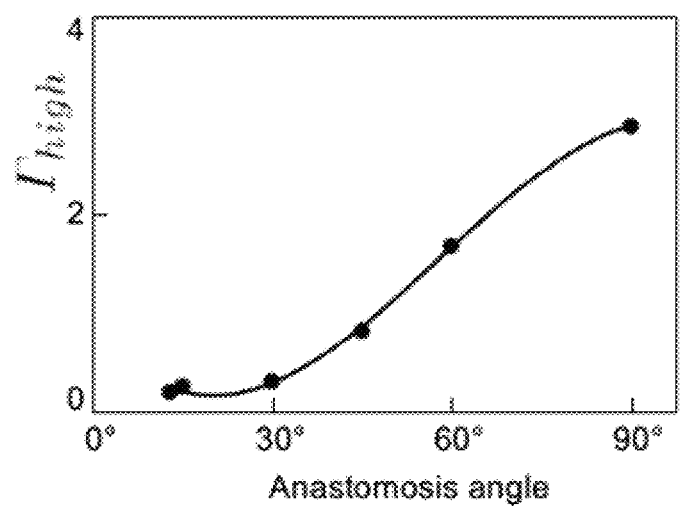

In order to further analyze the various attachment angles, two metrics were defined to quantify the degree to which each venous-end anastomosis angle disrupted the flow pathologically. As described above, for shear strain rates in the 50 histogram bins of the pathologically low range, $\Gamma_{low}$ was defined as the sum of a term that was the product of the inverse of the shear strain for a bin ($1/\dot{\gamma}_n$) and the area fraction $\varnothing_n$ for that bin:

$$\Gamma_{low} = \dot{\gamma}_{min} \sum_{n=1}^{50} \frac{\varnothing_n}{\dot{\gamma}_n} \quad (13)$$

where the normalization of $\dot{\gamma}_{min}=1$ s$^{-1}$ represented the lowest shear strain rate of the series. For shear strain rates in the 2001 histogram bins of the pathologically high range, $\Gamma_{high}$ was defined as the sum of a term that was the product of the shear strain for a bin ($\dot{\gamma}_n$) and the area fraction $\varnothing_n$ for that bin:

$$\Gamma_{high} = \frac{1}{\dot{\gamma}_{max}} \sum_{n=1000}^{3000} \varnothing_n \dot{\gamma}_n \quad (12)$$

where the normalization of $\dot{\gamma}_{max}=3000$ s$^{-1}$ represented the highest shear strain rate of the series. The summary metrics showing the degree to which different anastomosis designs induced pathologically low shear strain rates and pathologically high shear strain rates at the vein wall are provided in FIGS. 13A and 13B. The summary metrics suggested that the fraction of vein wall area undergoing pathologically high shear strain rates diminished with decreasing the venous-end anastomosis angle, as indicated in FIG. 13A. On the contrary, the area of the vein wall which underwent pathologically low shear rates stayed low from 90° to 30° then increased rapidly, as shown in FIG. 13B. The data collected suggests that increasing the angle of attachment past 30° can lead to a rise in the area of the vein wall that experiences unhealthy high shear rate. Additionally, decreasing the angle to below 30° can lead to a rise in the area of the vein wall that experiences unhealthy low shear rate. Therefore, it was determined that a 30° venous-end anastomosis angle would present the healthiest shear rate environment.

Shear strain rate fields at the venous end anastomosis have a critical role in maintaining arteriovenous graft patency. Placing the graft at an optimal anastomosis angle can provide patients a strategy for enhanced graft patency following the graft implantation.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. An arteriovenous graft operable for attaching to a vein, the arteriovenous graft comprising:
   a biocompatible material forming the arteriovenous graft having an arterial anastomosis end and a venous anastomosis end, the arteriovenous graft operable to couple the vein at a venous anastomosis; and
   a lachrymiform indent formed into the surface of the graft adjacent the venous anastomosis end, wherein a plurality of grooves are formed within the lachrymiform indent,
   wherein the venous anastomosis between the venous anastomosis end of the arteriovenous graft and the vein is arranged at an angle from less than 90° to about 13°.

2. The arteriovenous graft of claim 1, wherein the angle of the venous anastomosis is tailored to reduce a vein wall area over which pathologically high and/or pathologically low shear strain rates occur.

3. The arteriovenous graft of claim 1, further comprising a plurality of grooves formed into a surface of the arteriovenous graft adjacent to the venous anastomosis end of the graft.

4. The arteriovenous graft of claim 3, wherein the plurality of grooves are micro-digit grooves.

5. The arteriovenous graft of claim 4, wherein the micro-digit grooves have a width of from about 0.5 mm to about 5.0 mm and a length of from about 1.0 mm to about 10 mm.

6. The arteriovenous graft of claim 3, wherein the plurality of grooves comprises three micro-digit grooves.

7. The arteriovenous graft of claim 1, wherein the lachrymiform indent has a length of from about 1 mm to about 15 mm.

8. The arteriovenous graft of claim 1, wherein the arteriovenous graft has a length of from about 50 mm to about 200 mm.

9. The arteriovenous graft of claim 1, wherein the arteriovenous graft has a diameter that tapers from the arterial anastomosis end to the venous anastomosis end, the arterial anastomosis end having a diameter from about 3 mm to about 5 mm and the venous anastomosis end having a diameter of from about 6 mm mm to about 10 mm.

10. The arteriovenous graft of claim 1, wherein the venous anastomosis end has a semi major axis of from about 15 mm to about 30 mm.

11. The arteriovenous graft of claim 1, wherein the venous anastomosis between the venous anastomosis end of the arteriovenous graft and the vein is arranged at an angle of about 30°.

12. A method of reducing the risk of graft thrombosis and extending patency of an arteriovenous graft, comprising:
attaching an arteriovenous graft having a venous anastomosis end and an arterial anastomosis end to a vein at a venous anastomosis; and
attaching the arterial anastomosis end of the arteriovenous graft to an artery at a second venous anastomosis,
wherein the arteriovenous graft comprises:
a plurality of grooves formed in a surface of the arteriovenous graft adjacent the venous anastomosis end; and
a lachrymiform indent formed into the surface of the graft adjacent the venous anastomosis end, wherein a plurality of grooves are formed within the lachrymiform indent, and
wherein the venous anastomosis between the venous anastomosis end of the arteriovenous graft and the vein is arranged at an angle of about 30°.

13. The method of claim 12, wherein the angle of the venous anastomosis and/or the placement of the plurality of grooves formed within the surface of the arteriovenous graft are tailored to reduce a vein wall area over which pathologically high and/or pathologically low shear strain rates occur.

14. The method of claim 12, wherein the plurality of grooves are micro-digit grooves.

* * * * *